United States Patent
Desjardins et al.

(10) Patent No.: US 11,647,957 B2
(45) Date of Patent: May 16, 2023

(54) ULTRASOUND PROBE

(71) Applicant: UCL Business LTD, London (GB)

(72) Inventors: Adrien E. Desjardins, London (GB);
Edward Zhiyi Zhang, London (GB);
Malcolm Finlay, London (GB); Paul Beard, London (GB); Ioannis Papakonstantinou, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/542,867

(22) PCT Filed: Jan. 8, 2016

(86) PCT No.: PCT/GB2016/050038
§ 371 (c)(1),
(2) Date: Jul. 11, 2017

(87) PCT Pub. No.: WO2016/113543
PCT Pub. Date: Jul. 21, 2016

(65) Prior Publication Data
US 2018/0028117 A1 Feb. 1, 2018

(30) Foreign Application Priority Data
Jan. 15, 2015 (GB) ..................... 1500641

(51) Int. Cl.
*A61B 5/00* (2006.01)
*A61B 8/00* (2006.01)
(Continued)

(52) U.S. Cl.
CPC .......... *A61B 5/6848* (2013.01); *A61B 5/0095* (2013.01); *A61B 8/12* (2013.01);
(Continued)

(58) Field of Classification Search
CPC ....... A61B 5/0095; A61B 8/461; A61B 8/488; A61B 8/4444; A61B 8/12; A61B 5/0035;
(Continued)

(56) References Cited

U.S. PATENT DOCUMENTS 5,074,642 A * 12/1991 Hicks ................... G02B 26/103
385/116
5,311,485 A * 5/1994 Kuzmenko ............ G01V 1/186
367/149

(Continued)

FOREIGN PATENT DOCUMENTS

EP 0247746 A1 * 12/1987 ........... A61B 18/245
WO 2014174305 A2 10/2014

OTHER PUBLICATIONS

Lee et al.; A parametric study of ultrasonic beam profiles for a linear phased array transducer; published on May 2020; IEEE Transactions on Ultrasonics, Ferroelectrics, and Frequency Control (vol. 47, Issue: 3, May 2000); pp. 644-650 (Year: 2000).*

(Continued)

*Primary Examiner* — Chao Sheng
(74) *Attorney, Agent, or Firm* — Harness, Dickey & Pierce, P.L.C.

(57) ABSTRACT

Provided herein is a probe for ultrasound imaging of tissue. The probe comprises an optical relay having an optically absorbing coating at the distal end of the probe for generating ultrasound from excitation light via the photoacoustic effect, wherein the generated ultrasound propagates as an ultrasound beam into the tissue; and an ultrasound receiver separate from the optical relay. The optical relay is configured to receive as input a time-varying spatial pattern of excitation light at the proximal end of the probe and to transmit the excitation light to the distal end of the probe to illuminate the optically absorbing coating in accordance with said time-varying spatial pattern, thereby generating (Continued)

ultrasound from the excitation light via the photoacoustic effect to propagate as a scanning ultrasound beam into the tissue. The ultrasound receiver is configured to receive reflections of the ultrasound from tissue. Such an ultrasound probe may be incorporated, for example, into a transseptal puncture needle.

24 Claims, 19 Drawing Sheets

(51) Int. Cl.
    *G10K 15/04*     (2006.01)
    *A61B 8/12*     (2006.01)
    *G10K 11/00*     (2006.01)
    *A61B 8/08*     (2006.01)

(52) U.S. Cl.
    CPC ............ *A61B 8/4444* (2013.01); *A61B 8/461* (2013.01); *A61B 8/488* (2013.01); *G10K 11/002* (2013.01); *G10K 15/046* (2013.01); *A61B 5/0035* (2013.01)

(58) Field of Classification Search
    CPC ... A61B 5/6848; G10K 15/046; G10K 11/002
    See application file for complete search history.

(56) References Cited

U.S. PATENT DOCUMENTS

| | | | | |
|---|---|---|---|---|
| 5,663,550 | A * | 9/1997 | Peng ................. | G06K 7/10643 235/462.39 |
| 2002/0058890 | A1* | 5/2002 | Visuri .................... | A61B 18/26 601/4 |
| 2003/0130657 | A1* | 7/2003 | Tom ........................ | A61B 8/06 606/47 |
| 2005/0131289 | A1* | 6/2005 | Aharoni ............. | A61B 5/02007 600/407 |
| 2008/0108867 | A1 | 5/2008 | Zhou | |
| 2009/0244272 | A1* | 10/2009 | MacAulay ......... | G02B 21/0028 348/76 |
| 2010/0113929 | A1* | 5/2010 | Yeh .......................... | A61B 8/06 600/443 |
| 2011/0066023 | A1* | 3/2011 | Kanayama ........... | A61B 8/5238 600/407 |
| 2011/0251490 | A1* | 10/2011 | Aharoni ............. | A61B 5/02007 600/459 |
| 2013/0096413 | A1* | 4/2013 | Ashkenazi ......... | G01N 29/0654 600/407 |
| 2013/0303909 | A1* | 11/2013 | Kang .................... | A61B 5/0095 600/443 |
| 2013/0340232 | A1* | 12/2013 | Akkaya ................. | G01H 9/004 29/428 |
| 2014/0180032 | A1 | 6/2014 | Millett | |

OTHER PUBLICATIONS

Ashkenazi et al.; "Ultrasound Detection Using Polymer Microring Optical Resonator", Applied Physics Letters, vol. 85, No. 22, Nov. 29, 2004.
Biagi et al.; "Efficient Laser-Ultrasound Generation by Using Heavily Absorbing Films as Targets", IEEE Transactions on Ultrasonics, Ferroelectrics, and Frequency Control, vol. 48, No. 6, Nov. 2001.
Biagi et al.; "Fiber Optic Broadband Ultrasonic Probe for Virtual Biopsy: Technological Solutions", Hindawi Publishing Corporation, Journal of Sensors, vol. 2010, Article ID 917314, 6 pages, doi:101155/2010/0917314.
Buma et al.; "A High-Frequency, 2-D Array Element Using Thermoelastic Expansion in PDMS", IEEE Transactions on Ultrasonics, Ferroelectrics, and Frequency Control, vol. 50, No. 9, Sep. 2003.
Belsito; Design and Fabrication of MOMS-Based Ultrasonic Probes for Minimally Invasive Endoscopic Applications, Alma Mater Studiorum, University of Bologna, 2011.
Hou et al. "Broadband All-Optical Ultrasound Transducers", Applied Physics Letters 91, 073507 (2007).
Hou; "Broadband All-Optical Ultrasound Transducers for High-Resolution Ultrasound Imaging", A dissertation submitted in partial fulfillment of the requirements for the degree of Doctor of Philosophy, (Electrical Engineering), in the University of Michigan, 2008.
Hou et al.; Charaterization of a Broadband All-Optical Ultrasound Transducer—From Optical Ultrasound Transducer—From Optical and Acoustical Properties to Imaging, manuscript, accepted Jan. 28, 2008, IEEE Transactions on Ultrasonics, Ferroelectrics, and Frequency Control, vol. 55, No. 8, Aug. 2008.
Hou et al.; "Integrated all-optical ultrasound transducers" 2007 IEEE Ultrasonics Symposium.
Hsieh et al.; "All-optical scanhead for ultrasound and photoacoustic imaging—Imaging mode switching by dichroic filtering" Photoacoustics 2 (2014) 39-46.
Hsieh et al.; "All-Optical Transducer for Ultrasound and Photoacoustic Imaging by Dichroic Filtering" 10.1109/ULTSYM.2012.0352, 2012 IEEE International Ultrasonics Symposium Proceedings, 2012.
Li et al.; "Highly sensitive optical microresonator sensors for photoacoustic imaging", Photons Plus Ultrasound; Imaging and Sensing 2014, edited by Alexander A. Oraevsky, Lihong V. Wang, Proc. of SPIE, vol. 8943, 89430C, 2014.
Morris et al; "A Fabry-Perot fiber-optic ultrasonic hydrophone for the simultaneous measurement of temperature and acoustic pressure", J. Accoust. Soc. Am. 125 (6), Jun. 2009, 2009 Acoustical Society of America.
O'Donnell et al.; Optoacoustic generation of high frequency sound for 3-D ultrasonic imaging in medicine, Eur. Phys. J. Special Topics 153, 53-58 (2008) (c) EDP Sciences, Springer-Verlag 2008.
Sheaff, et al.; "Photoacoustic Imaging Endoscope", 31st Annual International Conference of the IEEE EMBS, Minneapolis, Minnesota, Sep. 2-6, 2009.
Sheaff et al.; "An All-optical Thin-film High-frequency Ultrasound Transducer", 2011 IEEE International Ultrasonics Symposium Proceedings.
Zhang et al.; "A miniature all-optical photoacoustic imaging probe" Photons Plus Ultrasound: Imaging and Sensing 2011, Proc. of SPIE vol. 7899.
Zou et al.; "Broadband miniature fiberoptic ultrasound generator", revised Jul. 4, 2014; accepted Jul. 8, 2014; published Jul. 18, 2014, Jul. 28, 2014; vol. 22, No. 15, Optics Express.
Acquafresca et al; "Toward Virtual Biopsy Through an All Fiber Optic Ultrasonic Miniaturized Transducer: A Proposal" IEEE Transacations on Ultrasonics, Ferroelectrics, and Frequency Control, vol. 50, No. 10, Oct. 2003, 0885-3010/$10.00 2003 IEEE.
Hou et al.; "An Integrated Optoacoustic Transducer Combining Etalon and Black PDMS Structures", IEEE Transacations on Ultrasonics, Ferroelectrics, and Frequency Control, vol. 55, No. 12, Dec. 2008, 0885-3010/$25.00 2008 IEEE.

* cited by examiner

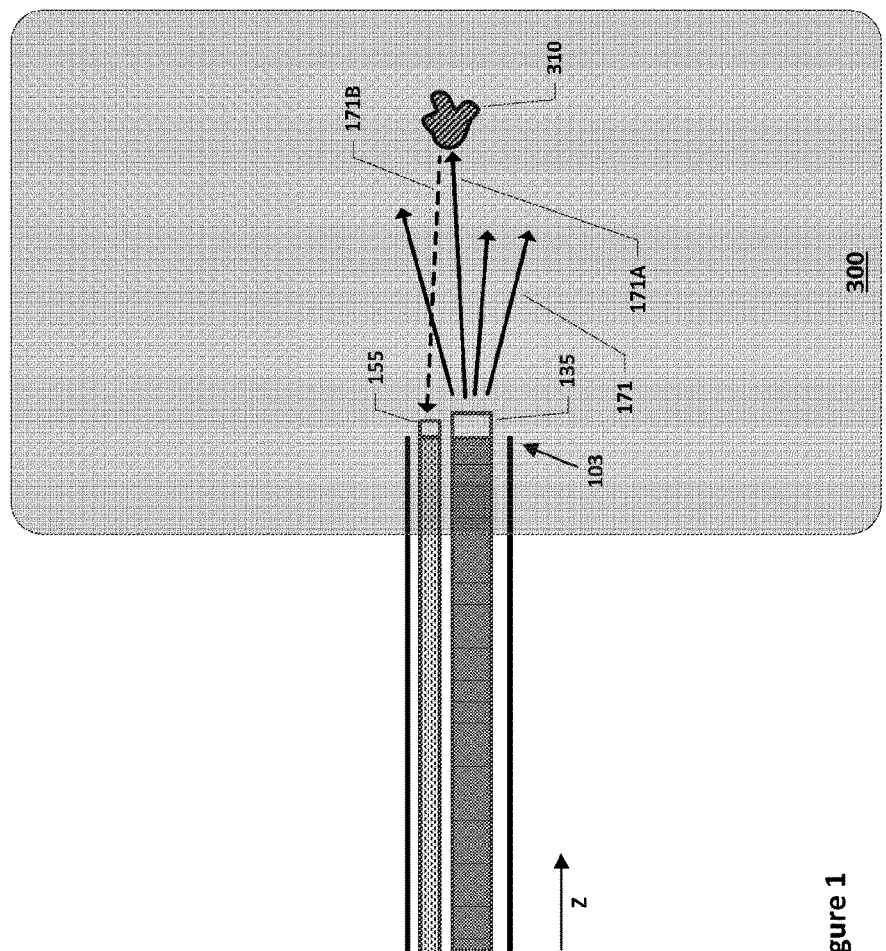
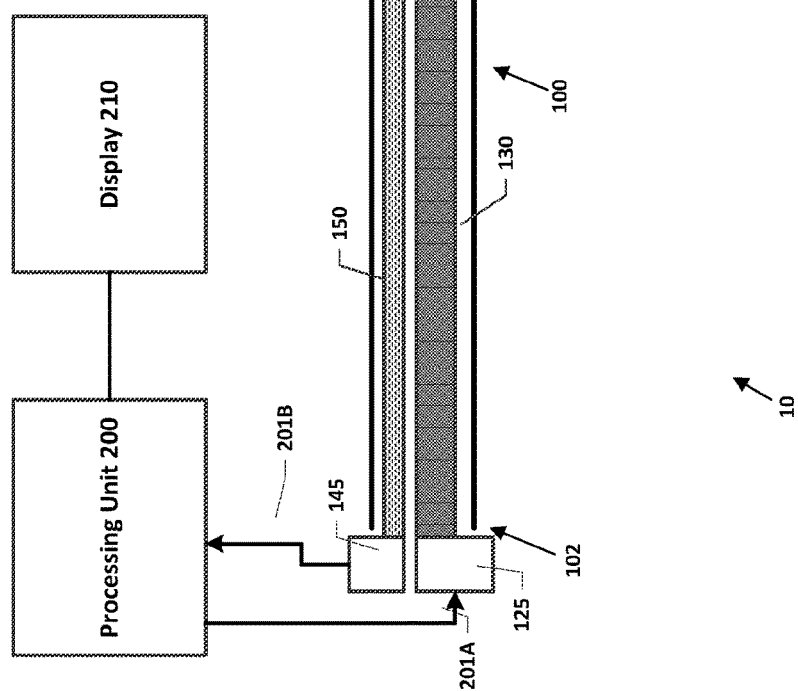
Figure 1

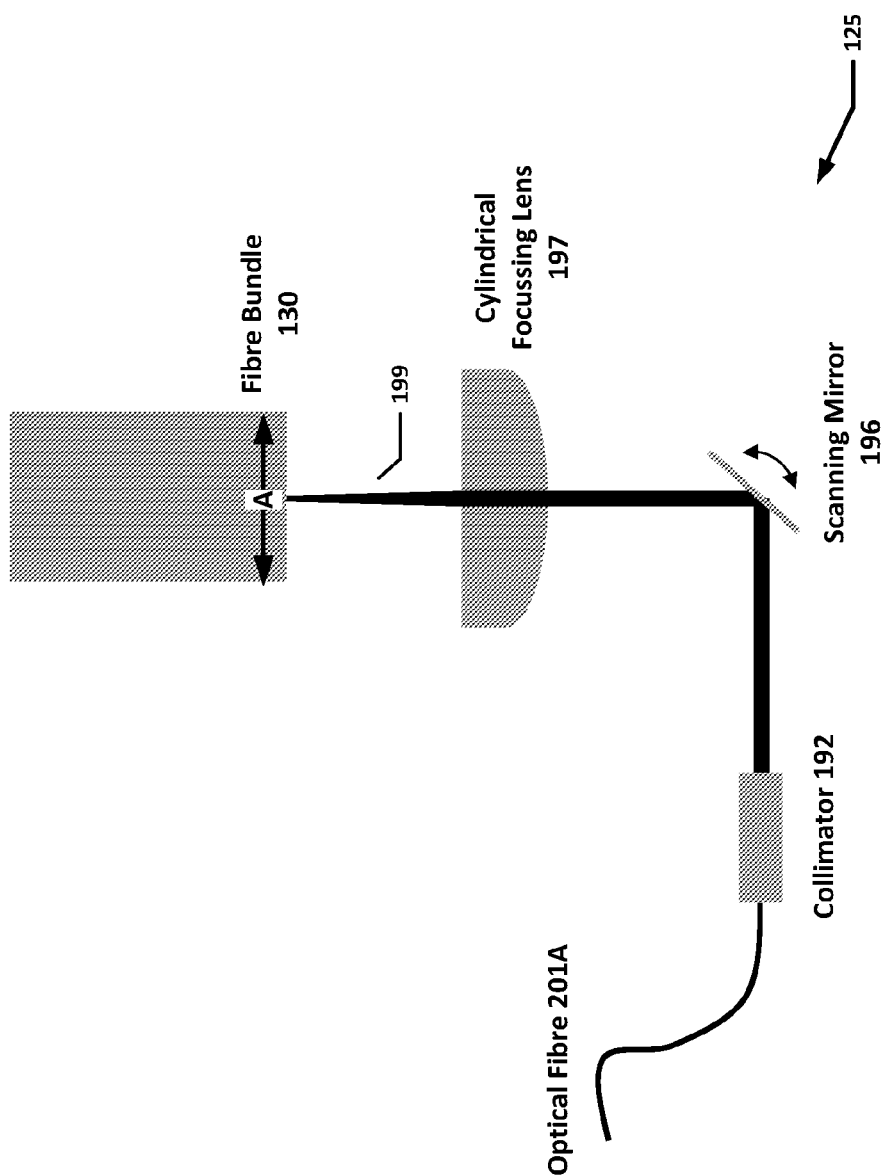

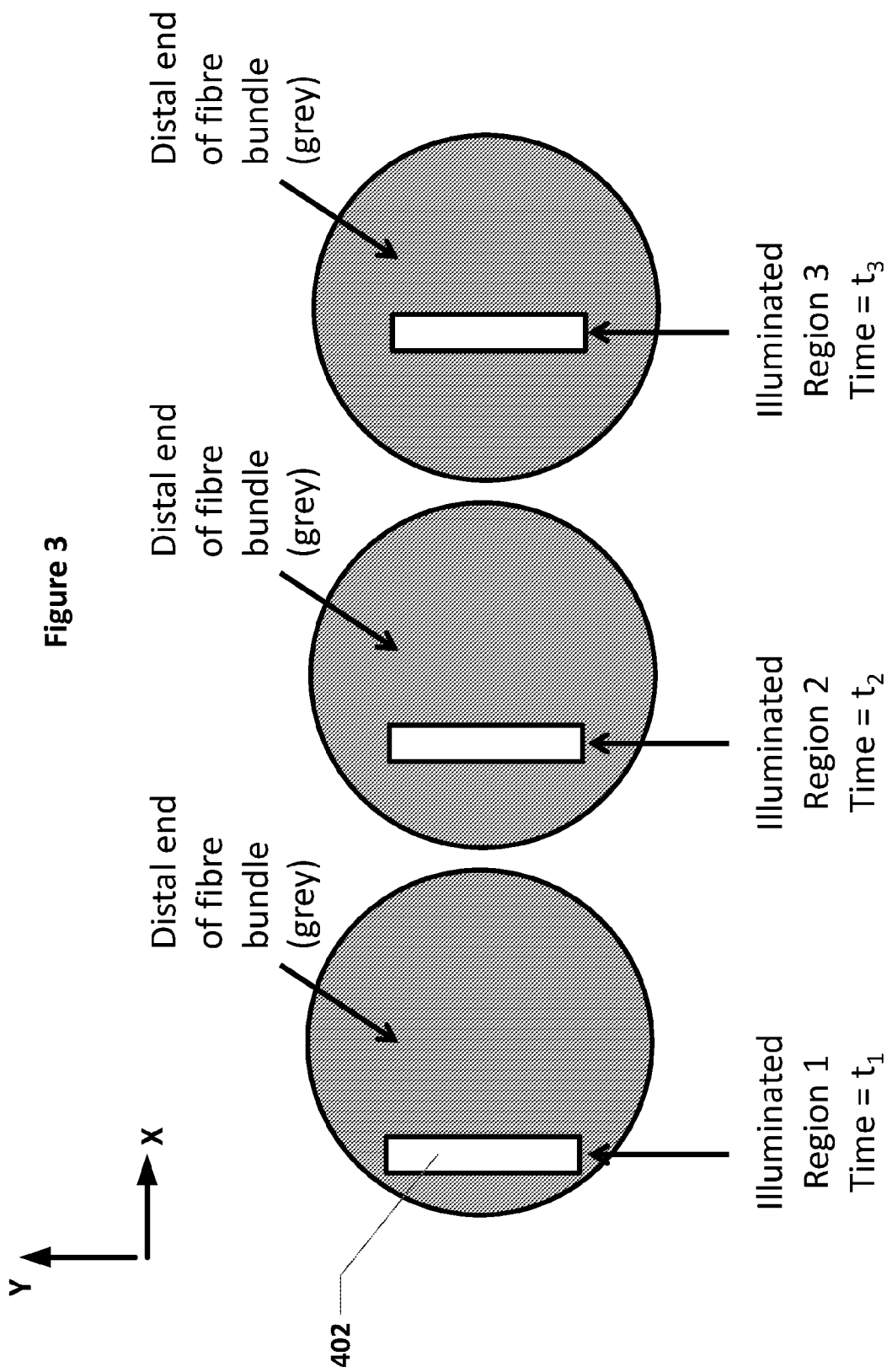

ULTRASOUND PROBE

FIELD OF THE INVENTION

The present invention relates to an ultrasound probe that uses excitation light to generate ultrasound via the photoacoustic effect.

BACKGROUND OF THE INVENTION

Miniature ultrasound imaging probes can provide information about tissue from within the body that is valuable for guiding minimally invasive procedures. For instance, intravascular ultrasound is used to visualise coronary artery plaque morphology during stent placement.

In present generation medical devices, ultrasound is generated and received electrically, typically using piezoelectric transducers or capacitive micro-machined ultrasonic transducers. The fabrication of broadband electrical transducers with millimetre-scale lateral dimensions and their integration into medical devices such as catheters with metre-scale longitudinal dimensions can be challenging and expensive.

Optical generation and reception of ultrasound are well-suited to sensing with miniature optical ultrasound probes. Both generation and reception can be performed with flexible optical fibres that are immune to EM radiation. These optical fibres can be produced inexpensively and do not require electronics at the distal end.

With optical generation of ultrasound, light is provided to an optically absorbing surface, and the thermal energy deposition results in an ultrasound wave via the photoacoustic effect. Such an absorbing surface can be positioned on a substrate with light provided by a free space optical beam (O'Donnell, 2008; Hou, 2007a; Hou, 2007b; Hou, 2007c; Zou, 2014), or the absorbing surface may be positioned at the distal end of an optical fibre (or multiple such fibres) with light provided by one or more optical fibre cores (Hou, 2008a).

For the optical reception of ultrasound, light is provided to an element that changes its optical properties when ultrasound waves impinge on it. For instance, optical reception of ultrasound can be performed with a Fabry-Pérot etalon positioned directly at the distal end of an optical fibre (Biagi, 2010; Zhang, 2011). Optical reception of ultrasound can also be performed with a micro-ring optical resonator (Ashkenazi, 2004; Hsieh, 2012; Hsieh, 2014).

In many clinical contexts it is desirable to generate two-dimensional (2D) or three-dimensional (3D) ultrasound images. For instance, a minimally invasive ultrasound probe inserted through the lumen of an endoscopic working channel may provide images of polyps. With current-generation medical devices, ultrasound image generation can be performed electrically by using a transducer element that is rotated and translated, with the scans then being concatenated to form an image, or by using a phased array. However, manufacturing such ultrasound probes can be challenging due to the miniaturisation of the electronics at the distal end.

Several designs for ultrasound sensors have been proposed that involve planar etalon sensors with two parallel reflective surfaces (Huang, 2007; Hou, 2008a; Hou, 2008b; Hou, 2008c; O'Donnell, 2008; Sheaff, 2009; Sheaff, 2011; Sheaff, 2014). These sensors allow for ultrasound measurements at different spatial positions on the etalon. A significant problem with this design is that the interrogation beam experiences walk-off which fundamentally limits the etalon finesse and thus the sensitivity for receiving ultrasound (Li, 2014). Huang et al. (2007) note that "the noise equivalent pressure is too high (820 kPa with a 30 MHz bandwidth)." Hou et al. (2008c) note that "extensive signal averaging of 1000 times is required at each detection array element". The total time required for image acquisition (e.g. a few hours) is therefore beyond what is currently available in a clinical context.

SUMMARY

The invention is defined in the appended claims.

Provided herein is a probe for ultrasound imaging of tissue. The probe comprises an optical relay having an optically absorbing coating at the distal end of the probe for generating ultrasound from excitation light via the photoacoustic effect, wherein the generated ultrasound propagates as an ultrasound beam into the tissue; and an ultrasound receiver separate from the optical relay. The optical relay is configured to receive as input a time-varying spatial pattern of excitation light at the proximal end of the probe and to transmit the excitation light to the distal end of the probe to illuminate the optically absorbing coating in accordance with said time-varying spatial pattern, thereby generating ultrasound from the excitation light via the photoacoustic effect to propagate as a scanning ultrasound beam into the tissue. The ultrasound receiver is configured to receive reflections of the ultrasound from tissue.

Also provided herein is a needle for performing transseptal puncture, said needle comprising: an optical relay having an optically absorbing coating at the distal end of the needle for generating ultrasound from excitation light via the photoacoustic effect, wherein the generated ultrasound propagates as an ultrasound beam into the tissue; an ultrasound receiver configured to receive reflections of the ultrasound from tissue; and a facility for measuring fluid pressure at the distal end of the needle.

BRIEF DESCRIPTION OF THE DRAWINGS

Various embodiments of the invention will now be described in detail by way of example only with reference to the following drawings:

FIG. 1 is a schematic diagram of an ultrasound system in accordance with some embodiments of the invention.

FIG. 1A is a schematic diagram of the electro-optic coupler from the ultrasound system of FIG. 1 in accordance with some embodiments of the invention.

FIG. 3 is a schematic diagram of using the ultrasound system of FIG. 1 to perform scanning in order to generate an ultrasound image in accordance with some embodiments of the invention.

DETAILED DESCRIPTION

Figure 1B:
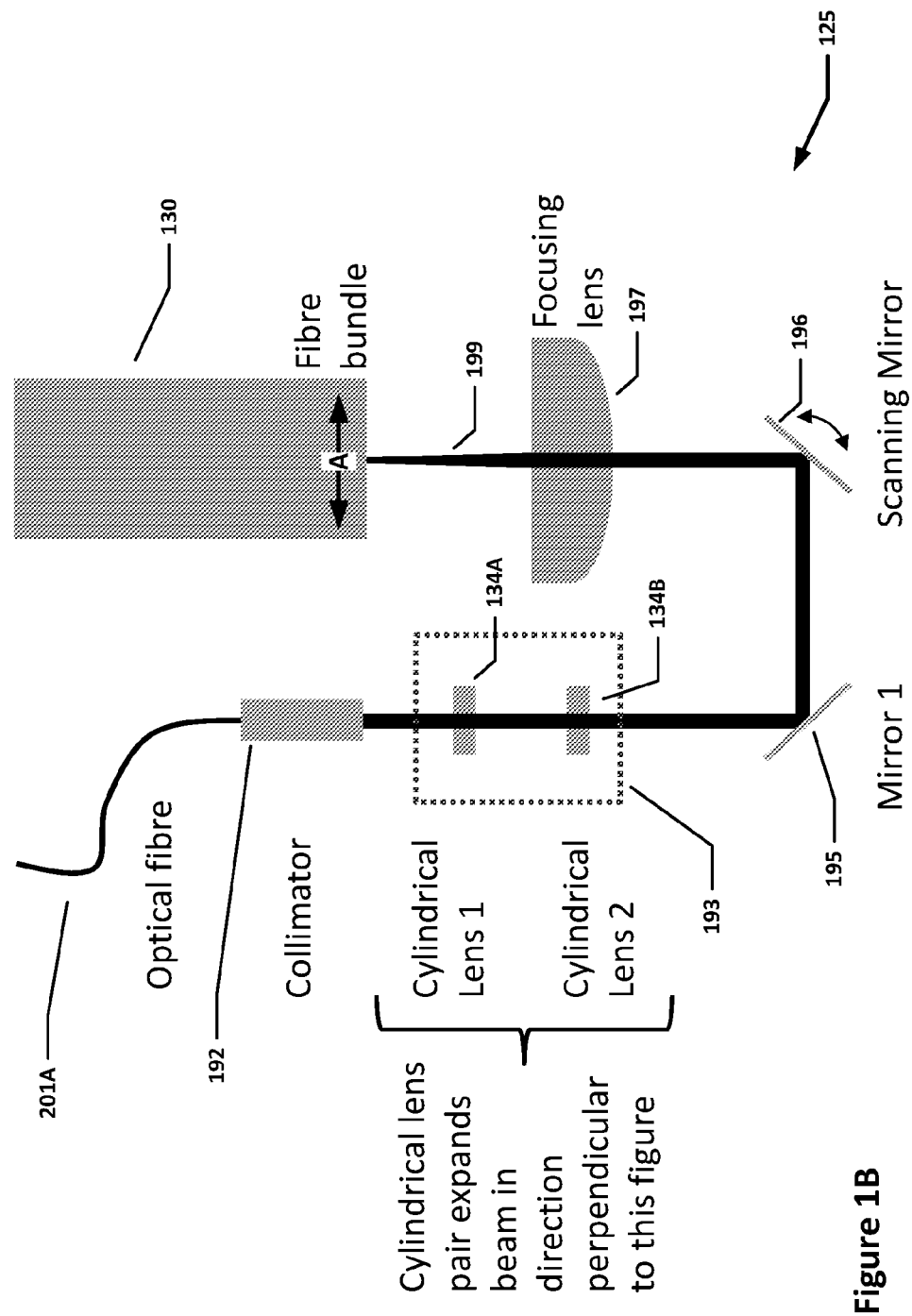
FIG. 1B is a schematic diagram of the electro-optic coupler from the ultrasound system of FIG. 1 in accordance with some other embodiments of the invention.

FIG. 1 is a schematic diagram of an ultrasound system 10 in accordance with certain embodiments of the invention. The main components of the ultrasound system are a processing unit 200 with an associated display monitor 210, and a medical instrument 100, such as a needle stylet or cannula, or an endoscopic probe. The medical instrument includes (incorporates, or has integrated into it) an optical fibre bundle 130 and an optical light guide 150. The processing unit 200 has two optical and/or electrical connections to the proximal end 102 of the medical instrument 100. The distal end 103 of the medical instrument is shown located in tissue 300 and includes a facility for generating and transmitting ultrasound into the tissue, and also an ultrasound receiver for receiving ultrasound from tissue. The arrow Z, which extends in the direction from the proximal end 102 to the distal end 103 of the medical instrument, can be considered as representing the primary or longitudinal axis of the medical instrument 100.

The first electrical connection 201A from the processing unit 200 to the medical instrument 100 is via a coupling device 125, e.g. an electro-optical coupler, to the optical fibre bundle 130. This electro-optical coupler 125 includes a light source for providing excitation light that has a time-varying spatial pattern in accordance with a control signal input from the processing unit 200. The optical fibre bundle 130 then acts as a form of optical relay to convey the illumination light from the proximal end to the distal end of the medical instrument. In some implementations, the optical relay may be provided as a different type of device (other than an optical fibre bundle), for example, as a multimode fibre that extends along the medical instrument.

In the implementation of FIG. 1, the optical fibre bundle 130 comprises a large number (e.g. more than 32, more than 64, more than 128, or more than 256) of optical fibres that extend along the length (longitudinal axis, Z) of the medical instrument 100. The number of optical fibres will be dependent on the size (and potentially cost) of the individual optical fibres, as well as the space available in the medical instrument 100 to accommodate the optical fibre bundle 130 (this space may vary according to the medical context and intended application).

The processing unit 200 uses the first connection 201A to transmit an optical or electrical control signal to the coupling device 125 which converts the control signal into a spatial pattern of light for transmission along the optical fibre bundle 130. This spatial pattern can be considered as an image defined in a cross-sectional plane of the optical fibre bundle 130, i.e. normal or perpendicular to the longitudinal axis represented by arrow Z. The optical fibres of the optical fibre bundle 130 then act as pixels that sample the image in the cross-sectional plane—in effect, they are therefore driven by the electro-optical coupler 125 in accordance with this spatial pattern or image.

The spatial configuration of the fibres within the optical fibre bundle 130, in particular the positioning of the fibres within the cross-sectional plane of the optical fibre bundle 130, is substantially maintained along the length of the optical fibre bundle from the proximal end 102 to the distal end 103. In other words, the optical fibre bundle is coherent, in that a spatial pattern of illumination at the proximal end is replicated at the distal end. Accordingly, the spatial pattern of the image as received from the coupling device 125 is, in effect, transmitted by the optical fibre bundle from the proximal end 102 of the light fibre bundle to its distal end 103, which is provided with an optically absorbing coating 135 for generating and transmitting ultrasound into the tissue.

The image or spatial pattern of light that travels down the optical fibre bundle 130 to the distal end 103 is converted by the optically absorbing coating 135 into ultrasound waves 171 that propagate from the medical instrument 100 into the tissue 300. The light travelling down the optical fibre 130 may be pulsed or modulated in amplitude at ultrasonic frequencies (in addition to having or encoding the time-varying spatial pattern). The optically absorbing coating 135 absorbs this (pulsed or modulated) light, and the resulting thermal deposition creates ultrasound waves that travel into the tissue 300. The pulsed or modulated light can therefore be regarded as excitation light, since it causes the coating 135 to produce the ultrasound waves which go into the tissue 300.

The optically absorbing coating 135 may comprise an elastomer, for example, polydimethylsiloxane with integrated carbon nanotubes. The optically absorbing coating 135 may further comprise gold nanostructures integrated into a polymer (Zou, 2014), carbon black (Buma, 2003), or graphite (Biagi, 2001). In some implementations, the optically absorbing coating 135 may be applied directly onto the end of the optical fibre bundle 130. In other embodiments, as described below, a spacer may be located between the optically absorbing coating 135 and the end of the optical fibre bundle.

The spatial and temporal distribution of the ultrasound waves 171 emitted from the optically absorbing coating 135 can be controlled by the processing unit 200. In particular, the spatial distribution of the ultrasound waves 171 can be controlled by sending appropriate control signals over connection 201A to the electro-optical coupler 125 in order to produce a desired spatial pattern for the excitation light travelling down the optical fibre bundle 130 to illuminate and excite the optically absorbing coating 135. This spatial pattern of illumination then determines the spatial distribution of ultrasound waves 171 transmitted from the optically absorbing coating 135. Similarly, the processing unit 200 can control the temporal distribution of ultrasound waves 171 transmitted from the optically absorbing coating 135 by sending appropriate control signals to the electro-optical coupler 125 in order to produce a desired temporal/spatial pattern for the excitation light travelling down the optical fibre bundle 130. The combination of this temporal and spatial control can be used to perform scanning of an ultrasound beam formed by ultrasound waves 171 to synthesise a 2-D or 3-D ultrasound image of the tissue 300 as described below.

As illustrated in FIG. 1, ultrasound waves 171 transmitted from the optically absorbing coating 135 may be partially reflected by an anatomical structure 310 within the tissue 300, such as a tumour or the inner surface of a heart atrium. The reflected waves 171B may return towards the medical instrument 100 and impinge on an optical element 155 which is located at the distal end 103 of the optical light guide 150. This optical element 155 acts as a transducer or ultrasound receiver (e.g. hydrophone) to convert the ultrasound waves 171B that are incident on the optical element 155 into a corresponding optical signal which is propagated by the light guide from the distal end 103 to the proximal end 102 of the medical instrument 100. In particular, the optical element 155 responds to the magnitude and phase of the incident ultrasound waves, together with their variation in time (rather than any spatial distribution of these ultrasound waves), and produces an output signal accordingly. The optical signal which is then conveyed along the light guide 150 (or other form of optical relay) incorporates temporal modulation (variations) that derive from these temporal variations of the ultrasound waves 171B as incident on the optical element 155. This optical signal, in particular the modulations thereof, is then converted into an electrical signal by electro-optical coupler 145 for return to the processing unit 200.

The optical element 155 is separate from the optical fibre bundle 150, in particular, it is not integrated into the optical absorbing coating and typically has its own signal return path to the processing unit 200. In some embodiments, the optical element 155 comprises a Fabry-Pérot cavity, which receives an interrogation light beam via optical light guide 150 from the proximal end 102 of the medical instrument 100. The Fabry-Pérot cavity produces a reflected light beam (from the interrogation light beam), which passes back down the optical light guide 150 to the electro-optical coupler 145. With a judicious choice of the wavelength of the interrogation light, the amplitude of the reflected light beam is very sensitive to the size (cavity spacing) of the Fabry-Pérot cavity, and this spacing is in turn affected by ultrasound waves that are incident upon the optical element 155. Accordingly, the amplitude of the reflected light is modulated by the strength of these ultrasound waves that are incident upon the Fabry-Pérot cavity, and these modulations are received ultimately by processing unit 200 as a measure of the reflected ultrasound waves 171B.

The skilled person is aware of various possible implementations for the electro-optical coupler 145, see, for example, Morris et al. 2009. In one implementation, the electro-optical coupler 145 includes a fibre-coupled wavelength-tunable light source that provides light to the optical light guide 150 via a circulator; the light reflected from optical element 155 is provided to a photodetector. It will be appreciated that electro-optical coupler 145 may be a somewhat different type of device from electro-optical coupler 125 (which is described in more detail below), since generally the former may be used to perform an electrical->optical conversion, whereas the latter may be used to perform the reverse conversion. The optical element 155 may be isolated from ultrasound transmissions that would otherwise propagate directly to it from the optically absorbing coating 135, or at least, the distal end 103 is configured to that such direct ultrasound transmissions are significantly attenuated. In some embodiments, this isolation or attenuation is accomplished by positioning the optical element 155 in a metal hypotube, so that the optical element is recessed from the distal end of the hypotube. In some embodiments, alternative (or additional) isolation or attenuation is obtained by positioning the optically absorbing coating in a second metal hypotube, so that the coating 135 is recessed from the distal end of the second hypotube. In these embodiments, the hypotubes serve as ultrasound attenuators.

It can be appreciated that aside from the optical element 155, other components can be used for receiving ultrasound reflected from tissue 300, depending upon the circumstances of any given implementation. For example, in some embodiments, the ultrasound receiver may be a microring optical resonator, while in other embodiments the ultrasound receiver may comprise a piezoelectric material such as polyvinylidene difluoride (PVDF).

As with a conventional electrical ultrasound system, if a single pulse of ultrasound waves is transmitted into the tissue 300, then a series of echos are typically obtained, at delay times T1, T2, etc., compared with the transmission of the original pulse (assumed to be at time T=0). The echo at time T1 is a reflection from a structure within the tissue (such as structure 310) for which the ultrasound travel time from the transmitter (the optical absorbing coating 135) to the tissue and then back to the receiver (optical element 155) totals T1. If we assume that the speed of the ultrasound waves in the body is V, and that optical absorbing coating 135 and the optical element 155 are close enough together so as to be considered as spatially coincident at the distal end 103, then the depth (distance) D of a reflecting structure from the distal end 103 with a delay T1 is given by V/2T.

If a series of pulse-echo measurements are acquired and concatenated in a display, with the vertical axis representing depth into tissue and the horizontal axis representing time, an M-mode image is obtained. Such an M-mode image may be suitable for certain clinical applications but unsuitable for others. If it is required to obtain a conventional B-mode ultrasound image, in which the vertical dimension corresponds to depth in tissue and the horizontal dimension corresponds to the lateral position in tissue, and if the locations of the ultrasound receivers are fixed, then different spatial patterns of ultrasound in tissue must be generated. Different spatial patterns of ultrasound in tissue can be generated by means of different spatial patterns of illumination (excitation) of the optically absorbing coating 135 by the fibre bundle 130. Accordingly, during the acquisition of an ultrasound image, these spatial illumination patterns at the distal end of the optical fibre bundle 130 are varied in time, and ultrasound reflections are acquired by the ultrasound receiver 155 for each spatial illumination pattern. The received ultrasound reflections can then be processed to generate a 2- or 3-dimensional image of the tissue in which the medical instrument is located.

FIG. 1A is a schematic diagram of the coupling device 125 from the ultrasound system of FIG. 1 in accordance with some embodiments of the invention. This device 125 is an optical coupler, in which processing unit 200 (or some other component on its behalf) generates an optical signal using an excitation light source that is passed down an optical fibre 201A to the coupling device 125. The optical fibre 201A is linked to a collimator 192 that produces a parallel optical output which may be elongated in a direction perpendicular to the page. This optical beam is then reflected by a scanning mirror 196, which can be controlled by an appropriate electrical signal, and next passes through a cylindrical focussing lens 197. The scanning mirror 196 rotates about an axis that is also perpendicular to the plane of the page (and hence parallel to the direction of elongation of the light beam). In particular, by scanning the mirror 196 backwards and forwards, the position at which the light beam 199 enters the fibre bundle 130 can be altered back and forth, such as indicated by arrow A in FIG. 1A.

Note that the coupling device 125 of FIG. 1A is relatively simple, in that it supports beam focusing in along one dimension, and scanning also in that same direction (both parallel to arrow A). However, other implementations may support different and/or multiple forms of scanning, and have different shaped beams, etc. In some implementations, the light beam 199 may be directed onto an array of mirror cells such as a digital micromirror device. This can result in a spatial pattern which is binary in nature according to the setting of each individual mirror cell. Such a configuration may therefore be used to apply an arbitrary spatial pattern to the optical fibre bundle.

FIG. 1B is a schematic diagram of the coupling device 125 from the ultrasound system of FIG. 1 in accordance with some other embodiments of the invention. This device 125 is generally similar to the optical coupler of FIG. 1B, except that between the collimator 192 and the scanning mirror 196 are located (in sequence) a lens arrangement 193 and an additional mirror 195. The lens arrangement 193 is shown as comprising two cylindrical lenses 134A, 134B which may be used to elongate the beam in a desired direction (such as perpendicular to the page, as discussed above. The mirror 195 is used to direct the elongated beam from the lens arrangement 193 onto the scanning mirror 196, according to the particular geometry of the arrangement.

Figure 1C:
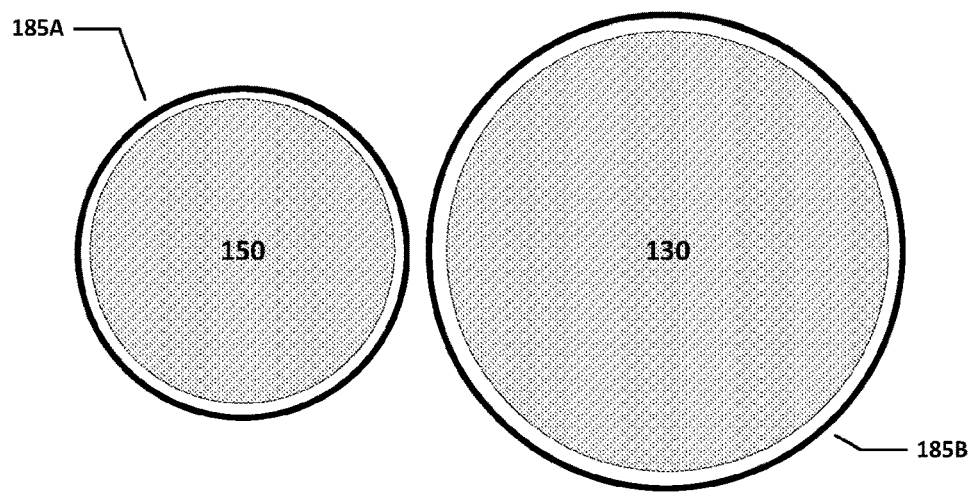
FIGS. 1C-1F are schematic diagrams of the cross-section at the distal end of a medical instrument for use as part of the ultrasound system of FIG. 1 in accordance with some embodiments of the invention.
Figure 1D:
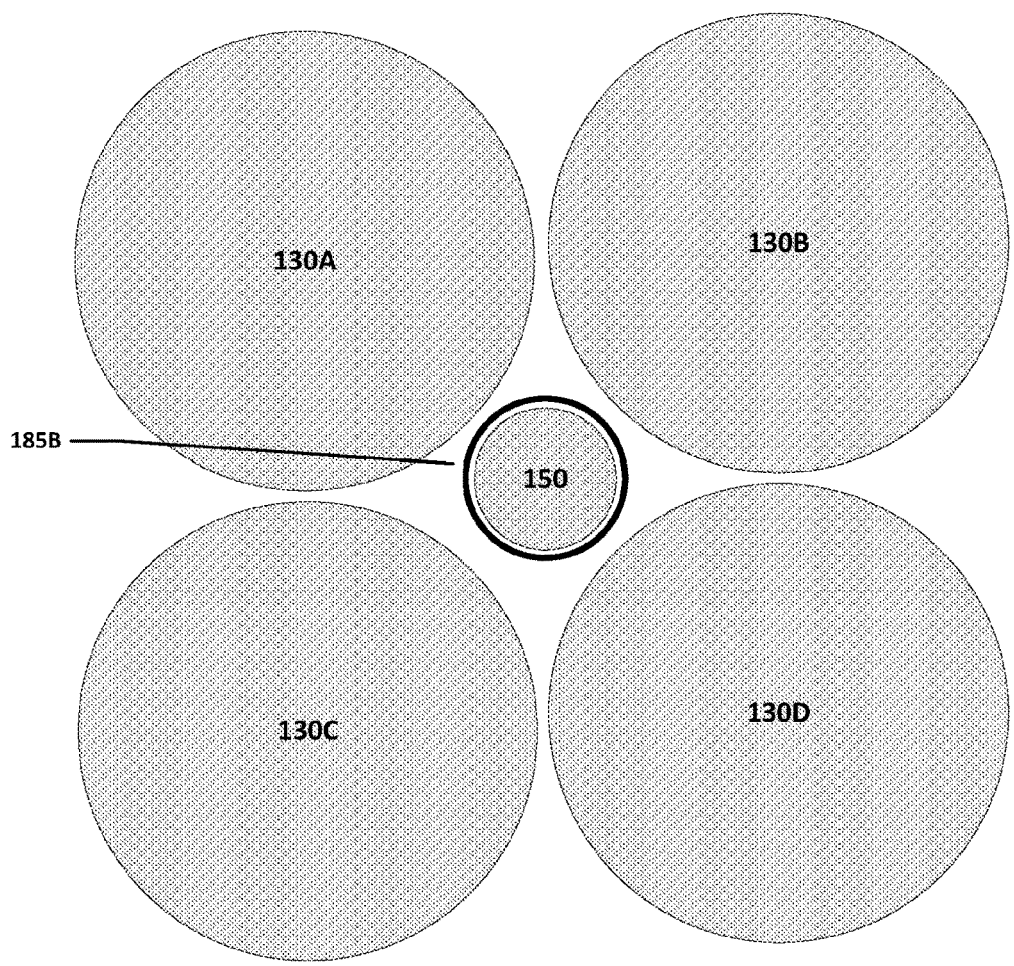
Figure 1E:
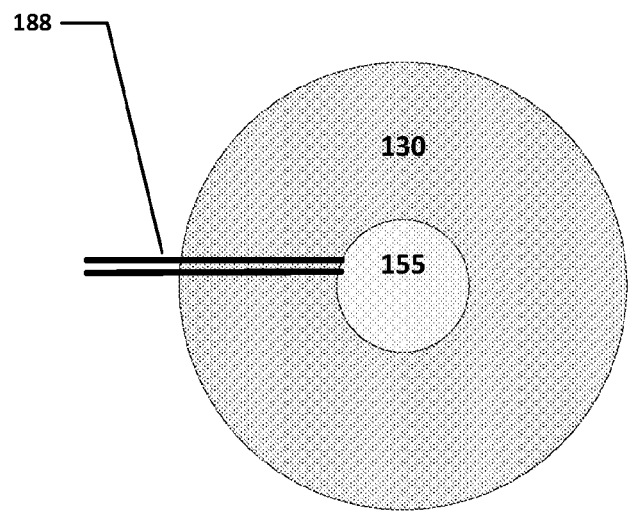

FIGS. 1C, 1D, 1E and 1E are four end views of the medical instrument, in effect looking back along the Z axis from the distal end 103 of the device, to show some example configurations of the fibre bundle 130 and the optical light guide 150. FIG. 1C illustrates a situation in which the optical fibre bundle 130 and the light guide 150 are located side-by-side along the medical instrument.

In addition, FIG. 1C shows that each of the optical fibre bundle 130 and the optical light guide 150 is surrounded, at least at the distal end 103, by an ultrasound attenuator—e.g. a metal hypotube 185A, 185B. The purpose of these metal hyptotubes is to reduce or prevent direct transmission of ultrasound from the optical absorbing coating 135 to the ultrasound receiver 155 (FIG. 1C does not show the optical absorbing coating 135 or the ultrasound receiver 155, but they are located at the end of the optical fibre bundle 130 and the optical light guide 150 respectively). In particular, the ultrasound signal of interest is based on the signal 171B reflected from tissue 300, since this encodes information about the tissue 300, including structures therein. In contrast, any direct transmission from the optical absorbing coating 135 straight to the ultrasound receiver 155 represents noise, which may be quite large in comparison with the level of signal 171B (since the optical absorbing coating 135 is relatively close to the ultrasound receiver 155). Accordingly, the presence of attenuators 185A, 185B helps to reduce the direct (noise) transmission, thereby improving the signal-to-noise ratio of the reflected ultrasound signal 171B. The hypotubes 185A, 185B are also useful for attenuating any ultrasound that reverberates within the distal end of the medical instrument.

In order to help with this attenuation, the optical absorbing coating may be slightly recessed into hypotube 185A—i.e. the hyptotube 185B extends further out towards the distal end 103 than the optical absorbing coating. Likewise, the ultrasound receiver 155 may be slightly recessed into hypotube 185B.

It will be appreciated that the configuration of FIG. 1C is provided by way of example, and many other configurations are feasible. For example, some implementations may omit one of the hypotubes 185A, 185B, if a single hypotube is found to provide adequate attenuation by itself. Another possibility is that the ultrasound attenuation is provided by a wall or other structure located between the optical fibre bundle 130 and the optical light guide 150 (rather than by a circular tube that completely surrounds one of these components).

FIG. 1D illustrates another configuration, in which the optical light guide 150 is provided with a hypotube 185B to act as an ultrasound attenuator, but not the optical fibre bundle 130. Note also that the optical fibre bundle 130 of FIG. 1D comprises four sub-bundles 130A, 130B, 130C and 130D, each of which is fibre bundle in its own right. The use of sub-bundles to form the overall optical fibre bundle 130 can provide an effective approach for increasing the number of individual fibres that are contained with the overall optical fibre bundle.

FIG. 1E illustrates another configuration, in which the ultrasound receiver 155 is located in front of the end of the optical fibre 130 (the optical absorbing coating 135, not shown in FIG. 1E, is also located at the end of the optical fibre 130). The ultrasound receiver 155 is provided with an electrical connection 188 for returning the received signal back along the medical instrument to the processing unit 200. In this configuration, the ultrasound receiver may be, for example, a PVDF ultrasound detector, as mentioned above.

Having the ultrasound receiver 155 located on the end of the optical fibre bundle 130, as shown in FIG. 1E, has some benefits in ultrasound signal detection. For example, it supports a minimal ultrasound signal travel distance (straight there and back), which helps to improve the strength of the received signal. In addition, the signal received as a result of scanning the ultrasound beam 171A (as described in more detail below) can be easier to interpret and process based on this geometry.

Figure 1F:
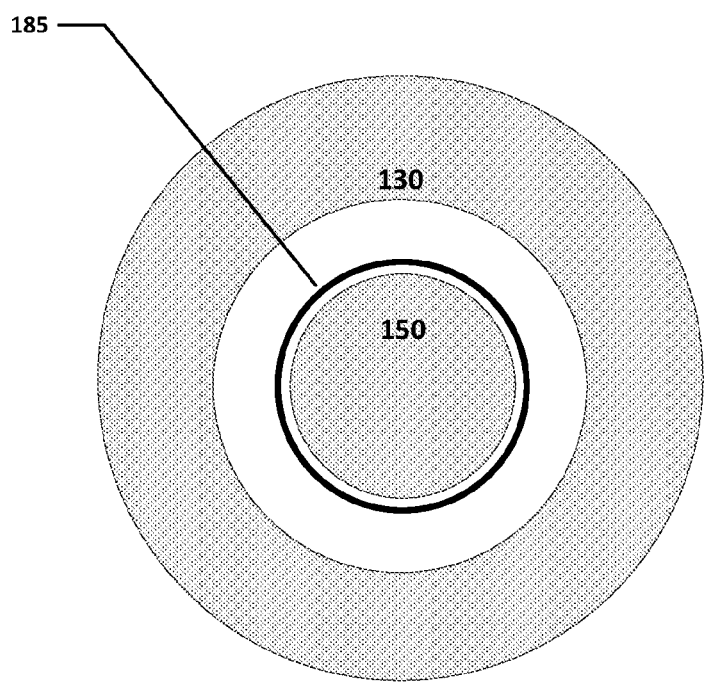

FIG. 1F shows another implementation which has a similar geometry to that shown in FIG. 1E. However, in FIG. 1F, the optical fibre bundle 130 has an annular arrangement, with in the optical light guide 150 then being inside, and coaxial with, the optical fibre bundle. (As for FIG. 1C, FIG. 1F does not show the optical absorbing coating 135 or the ultrasound receiver 155, but they are located at the end of the optical fibre bundle 130 and the optical light guide 150 respectively). Note that in this implementation, the optical light guide 150 is provided with an attenuator 185 to reduce direct transmissions, as described above.

It will be appreciated that the implementations shown in FIGS. 1-1F are provided by way of example, and the skilled person will be aware of many potential modifications and variations. In addition, features from the different examples can be combined with one another as appropriate, depending upon the circumstances of any given implementation.

Figure 2:
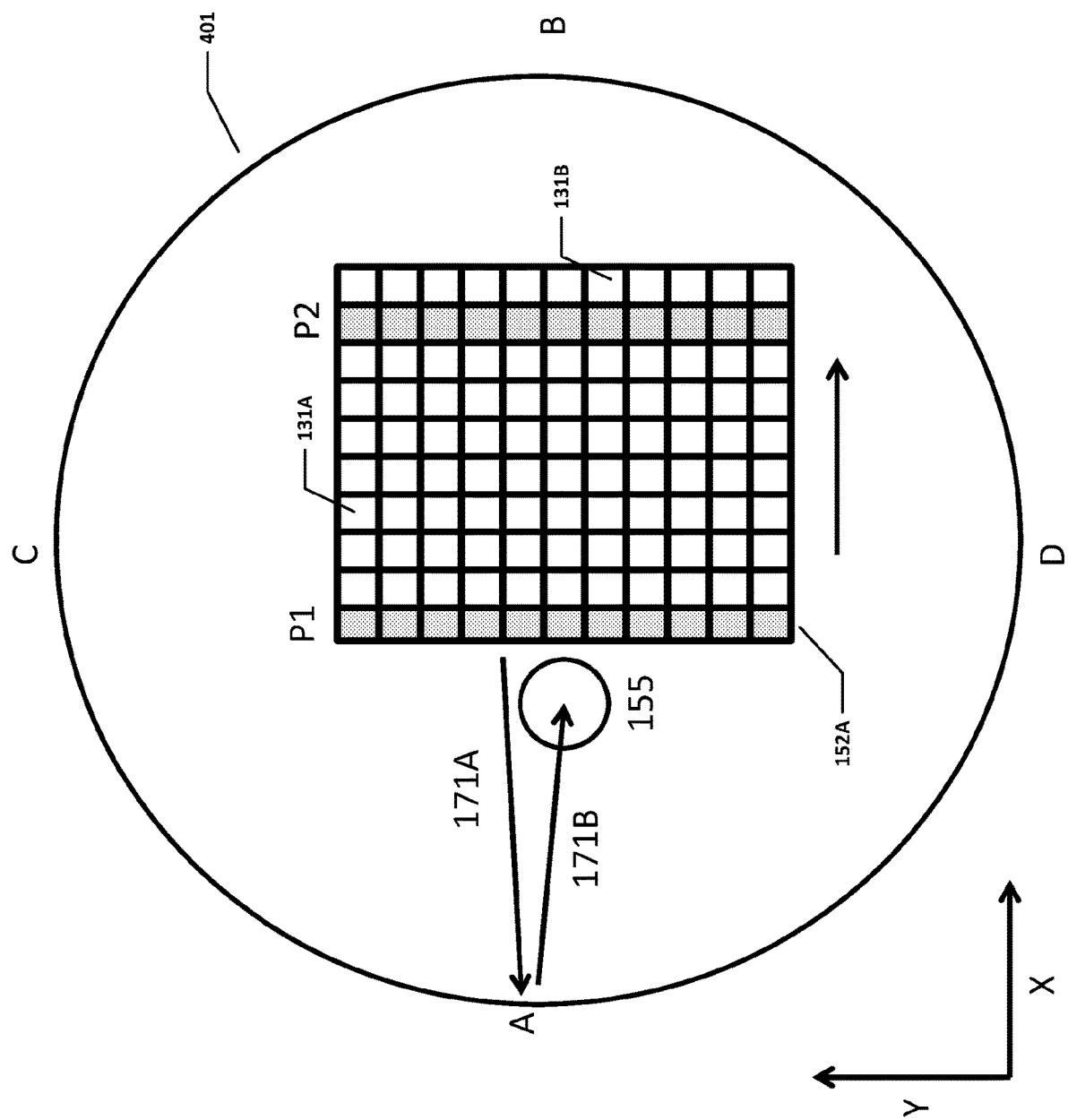
FIG. 2 is a schematic diagram of using the ultrasound system of FIG. 1 to perform scanning in order to generate an ultrasound image in accordance with some embodiments of the invention.

FIG. 2 is a schematic diagram illustrating how the ultrasound system 10 can acquire directional information for a reflective structure, such as tissue structure 310, by applying a time-varying spatial pattern of illumination to the fibre bundle 130 (and hence to the optically absorbing coating 135). Thus FIG. 2 shows a cross-section of the fibre bundle 130 which comprises multiple individual fibres 131A, 131B, etc. For ease of exposition, the fibre bundle is shown as having a rectangular (nearly square) cross-section, with a rectangular array of fibres corresponding to the X and Y axes as illustrated in FIG. 2, which will be referred to as the row and column directions respectively. (The X and Y axes are in a plane normal to the longitudinal Z axis shown in FIG. 1).

The processing unit 201 is able to control the coupling device 125 so as to illuminate a particular spatial pattern of fibres 131 with the fibre bundle 130 (which can be changed with time). Thus in FIG. 2, one column 152A (i.e. extending parallel to the Y-axis) of fibres 131 is shown illuminated. It will be appreciated that such an elongated beam pattern might be achieved with the coupling device shown in FIG. 1A or 1B. The remaining fibres, i.e. all the fibres apart from column 152A, are not illuminated. This initial pattern of illumination, in particular, the position of the illuminated column 152A, is referred to as P1. The processing unit 201 is able to scan this column of illumination across the fibre bundle, starting at position P1, and ending at the position P2. This scanning is achieved by illuminating each column of the fibres in turn. Again it will be appreciated that such scanning in the direction of the arrow shown in FIG. 2 can be achieved using the coupling device shown in FIG. 1A or 1B (in which the arrow of FIG. 2 is generally parallel to the arrow A of FIGS. 1A and 1B).

FIG. 3 shows another example of this scanning an elongated feature 402 of illumination across the distal end of the fibre bundle, where the direction of scan (X) is perpendicular to the direction of elongation (Y). In particular, FIG. 3 shows the progression of the scan, starting at time $T_1$, where region 1 is illuminated, proceeding to time $T_2$, where region 2 is illuminated, and then time $T_3$, where region 3 is illuminated. It can be seen therefore that this scan is accomplished by changing the pattern of illumination with time, such that the feature 402, which corresponds to the currently selected fibres for illumination, scans across the cross-section of the fibre bundle. Note that this scanning is generally based on a sequence of pulses, where each pulse is short—typically 50 ns or less. Thus one or more pulses are generated to illuminate region 1, followed by one or more pulses to illuminate region 2, and so on, until the scan has been completed across the surface of the optical fibre bundle 130.

For any individual pulse, the spatial illumination pattern of FIG. 3 may comprise an ellipsoidal feature 402 (for simplicity, this ellipsoidal shape is approximated by a rectangle in FIG. 3). The scan effectively generates a sequence of multiple such ellipsoidal features 402 in positions that are translated incrementally in one direction (X) across the distal end of the optical fibre bundle. Each of the ellipsoidal features is elongated so as to be significantly longer in the dimension (X) perpendicular to translation, than in the dimension (Y) parallel to translation. As one example, for a circular optical fibre bundle 130 that is 3 mm in diameter, the axes of the ellipsoids in a direction parallel and perpendicular to the direction of translation may be 30 microns and 1 mm respectively.

Returning to FIG. 2, this also includes a circle that represents a portion 401 of a spherical shell of ultrasound propagation from the fibre bundle 130 corresponding to a given travel (echo) time from the distal end of the medical instrument. (FIG. 2 makes the physically plausible assumption that the ultrasound waves from the optically absorbing coating 135 travel very approximately in a forward direction, thereby defining the portion of the spherical shell of interest).

If ultrasound waves 171 are generated by providing excitation light to all of the fibres 131 of fibre bundle 130, i.e. without applying a spatio-temporal pattern (or, equivalently, if there is only a single fibre in the fibre bundle), then the timing of the reflected ultrasound waves 171B from a tissue structure provide a distance estimate to this structure, but no directional information—i.e. the structure merely is located somewhere on the portion 401 of a spherical shell with a radius corresponding to this distance estimate. However, applying a time-varying spatial pattern to the fibre bundle 130 allows such directional information to be obtained.

FIG. 2 illustrates four potential locations on the shell as A, B, C, D. FIG. 2 further illustrates ultrasound waves 171A propagating to location A from position P1 (more accurately, from the optically absorbing coating corresponding to position P1 in the fibre bundle 130), and then reflected ultrasound waves 171B returning from location A to the optical element 155. It will be appreciated that as the column of illumination is scanned from position P1 to position P2, the propagation time for ultrasound 171A steadily increases, whereas the propagation time for ultrasound waves 171B is unchanged (the positions of the tissue structure at A and the optical element 155 remain constant). Accordingly, the overall timing for the echo delay increases as the scan column goes from position P1 to P2 (based on the increased propagation time for ultrasound waves). Conversely, for a tissue structure located at position B, the opposite effect would be observed, namely the overall timing for the echo delay would decrease as the scan column goes from position P1 to P2.

It can be seen therefore that scanning the column of illumination from P1 to P2 gives an indication of the positioning of a reflective structure in terms of its X-coordinate, i.e. in a dimension parallel to the scan direction. Note that since the ultrasound travel time is also known, this defines in effect the depth direction (Z-axis). Therefore scanning such as shown in FIGS. 2 and 3 creates, for a first scan direction, an image plane that contains the longitudinal axis X and the scanning direction.

The processing unit 200 may also be able to control the optical fibre bundle 130 to provide a row of illumination, i.e. extending parallel to the X-direction, which is scanned in the Y direction. The resulting change of timing from scanning in this direction gives an indication of the positioning of a reflective structure in terms of its Y-coordinate. Combining the X-coordinate and the Y-coordinate then allows the location of the reflecting structure within the shell portion 401 to be determined. Furthermore, this X-Y positioning, in conjunction with the known overall delay timing, which determines the distance from the distal end 103, allows the full three-dimensional location of a reflecting structure such as tissue structure 310 to be determined (and hence a corresponding 3-D image to be derived).

Although FIG. 2 depicts the fibre bundle 130 as having an approximately square cross-section, it will be appreciated that many cross-sections could be utilised, for example, circular, elliptical, rectangular, hexagonal, or other more irregular shapes. It is also possible to use an annular configuration, such as shown in FIG. 1F, where the central (axial) opening inside the fibre bundle provides space for some other component (e.g. optical light guide 150, or a fluid channel as described below in relation to a transseptal puncture needle) to extend from the proximal end 102 to the distal end 103 of the medical instrument 100. The fibre bundle 130 may also have some form of linear arrangement, wherein the individual fibres are arranged in a line or sequence (the line may then be folded or curved to create a pattern extending into two-dimensions).

Figure 4B:
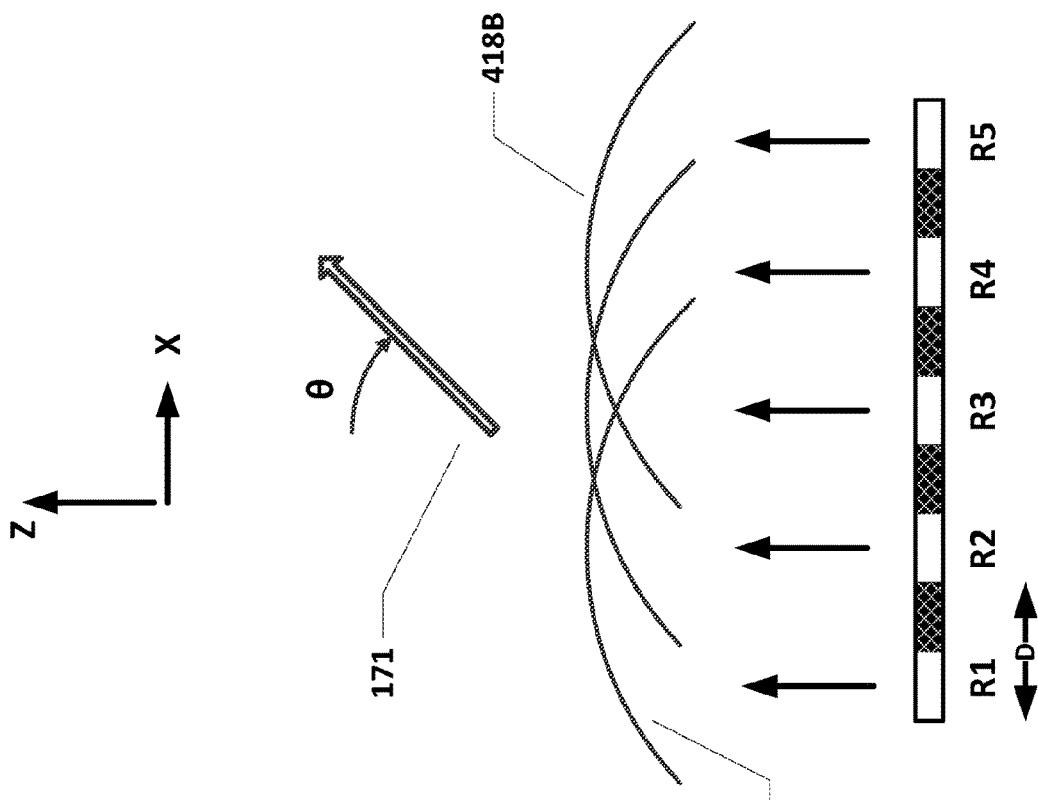
FIGS. 4A and 4B are schematic diagrams of using the ultrasound system of FIG. 1 to perform scanning by ultrasound steering in order to generate an ultrasound image in accordance with some embodiments of the invention.
Figure 4A:
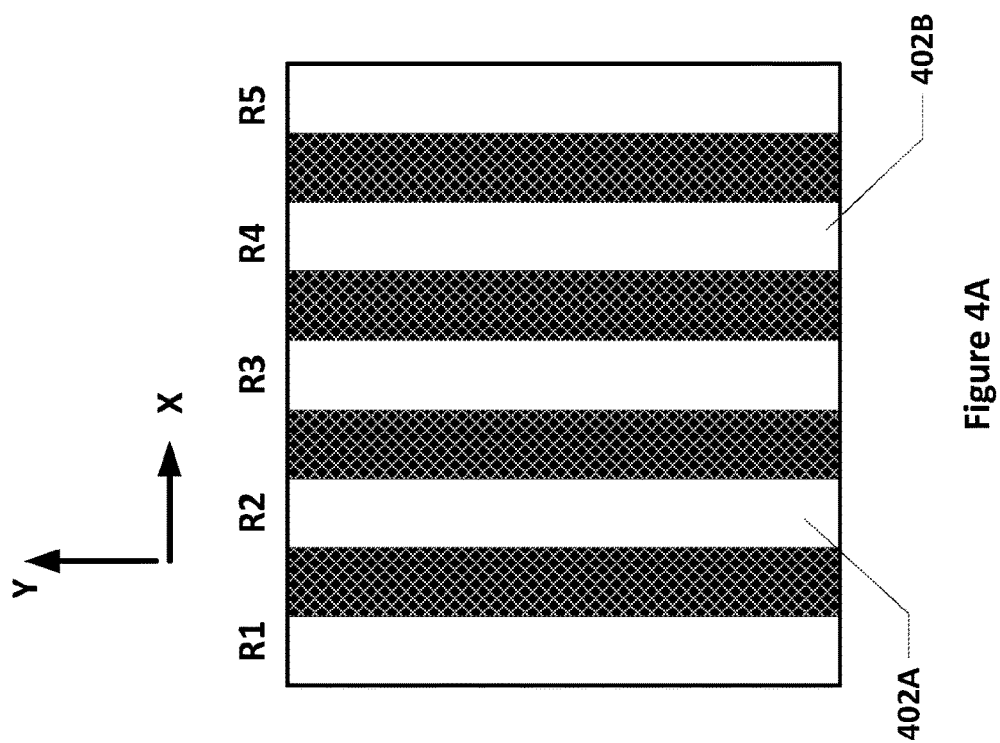

FIG. 4 illustrates another example of using the fibre bundle 130 to perform scanning of the ultrasound beam in which multiple elongated regions (columns) 402A, 402B are illuminated at the same time. In particular, FIG. 4A shows the X-Y plane with a pattern of excitation of the coating 135 in which columns R1, R2, R3, R4 and R5 are illuminated at the same time. FIG. 4B shows the corresponding X-Z plane and illustrates ultrasound wavefronts propagating out from each elongated region. (For simplicity FIG. 4B shows only a single wavefront from regions R2, R3 and R4, but it will be appreciated that there will be a succession of wavefronts from each of regions R1, R2, R3, R4 and R5).

The propagating wavefronts shown in FIG. 4B result in an interference pattern between the signals from the different regions R1, R2, R3, R4 and R5. If the physical spacing between columns R1, R2, R3, R4, R5 is D, as indicated in FIG. 4B, the wavelength (in tissue) of the ultrasound radiation is $\Lambda$ (assuming all regions R1, R2, etc have the same excitation frequency), and we apply a phase offset of $\varphi$ between the excitation signal of successive columns, so that R1 can be considered as having 0 (zero) offset, R2 a phase offset of $\varphi$, R3 a phase offset of $2\varphi$, R4 a phase offset of $3\varphi$, and R5 a phase offset of $4\varphi$, then the configuration of FIG. 4B acts as a phased array. As is known in the art, such a phased array produces constructive interference and a resulting ultrasound beam 171 at an angular direction $\theta$ measured from the normal for $\sin \theta = (\lambda/2\pi D)(\Delta\varphi \pm 2\pi n)$, where n is any integer.

The phased array system can scan the beam 171 through different angles of $\theta$ by changing the phase offset $\varphi$ and/or the wavelength $\lambda$ of the excitation signal as appropriate. In effect, this rotates the ultrasound beam 171 about the Y axis. For example, if $\varphi=0$, then $\theta$ is likewise zero, so that the primary (n=0) ultrasound beam 171 propagates in the normal direction. If $\varphi$ is slowly increased, this will result in a corresponding increase in $\theta$, thereby scanning the beam 171 away from the normal.

It will be appreciated that although FIG. 4 illustrates the use of illumination features that are elongated in a column direction to generate an ultrasound beam having a direction of propagation which is perpendicular to the Y axis, we could also use instead illumination features that are elongated in a row direction for a beam having a direction of propagation which is perpendicular to the X axis. It also possible to use elongated features that extend in any intermediate direction between the X and Y directions to produce an ultrasound beam having a corresponding intermediate direction of propagation.

Although FIG. 4 has been described as having a constant phase offset between adjacent columns across the whole array of the fibre bundle 130, other implementations may adopt a more complex approach. For example, if we have columns R1 . . . R15, then the phasing of columns R1-R5 may be arranged to produce a beam 171 at an angle of $\theta+\Delta\theta$, the phasing of columns R6-R10 may be arranged to produce a beam 171 at an angle of $\theta$, and the phasing of columns R10-R15 may be arranged to produce a beam 171 at an angle of $\theta-\Delta\theta$, where $\Delta\theta$ is small in comparison with $\theta$. This in effect results in an overall beam which is slightly converging towards a focus at a distance from the distal end 103 which is determined by $\Delta\theta$. Such a converging beam can be useful, inter alia, for providing increased ultrasound power (and hence stronger reflections) at a given depth location in the tissue. Conversely, if $\Delta\theta$ is arranged to be negative, then a slightly diverging beam is produced, which can be useful, inter alia, for giving a wider field of view. In either case (for converging or diverging), the beam can still be scanned as discussed above by changing the primary or central direction ($\theta$) of the beam $\theta$. The skilled person will be aware of additional beam shapes and scanning patterns that can be implemented using a phased array approach.

Accordingly, the device 10 may implement one or more of a number of different scanning modes or mechanisms. Thus there may be a linear translational scan, such as shown in FIGS. 2 and 3, effectively in a plane perpendicular to the primary, i.e. (central, main or average) outward direction of propagation of the ultrasound waves 171 from the distal and 103. There may be first and second such linear translational scans, which are orthogonal to one another, to provide information in different dimensions. Also, multiple such linear translational scans may be implemented at a number of different angles (not just two orthogonal directions). Another possibility is that there is a scan by rotating the ultrasound beam about an axis which is perpendicular to the primary outward direction of propagation ($\theta$), such as shown in FIG. 4. Note that there may be only one such axis of rotation, or two or more axes of rotation may be used in succession (lying in a plane perpendicular to the primary outward direction of propagation).

Other possible scanning patterns include having an elongated beam 402 such as shown in FIG. 3, but rather than performing a linear translational scan, instead rotating the elongated beam about an axis of rotation which is parallel to the primary outward direction of propagation (i.e. rotating about the axis which is normal to the X-Y plane, i.e. about the z-axis). In addition, other spatial patterns may be utilised, instead of just an elongated beam. For example, the spatial pattern may comprise a circular annulus, which is expanded outwards in radius in order to perform the scanning. In addition, various scanning patterns (modes) may be applied in sequence.

Another possibility is that the illumination light is provided to individual fibres of the optical fibre bundle sequentially with a raster-scanning pattern. In this embodiment, the illumination region is defined by the spatial region of the optically absorbing coating that receives illumination light from an individual optical fibre, which can be substantially circular. In a variation of this embodiment, a small number (greater than one, for instance 7) of optical fibres are illuminated at each time.

Another possibility is that the intensity of the illumination light is varied across different spatial patterns, so that one illumination pattern can be used for generating an ultrasound image, and a second illumination pattern at a subsequent point in time can be of higher intensity to generate ultrasound with higher pressures. The latter illumination pattern can be used, for instance, to ablate tissue with the principle of high intensity focused ultrasound. In any event, the spatial pattern that is applied to the optical fibre bundle 130 is varied in time to cause the scanning of the ultrasound beam with which to generate ultrasound image. This scanning generally involves changing the direction of the ultrasound beam (e.g. by steering) and/or shifting the location of the ultrasound beam (such as shown in FIG. 3), and/or changing the profile of the beam (as opposed to moving a beam of constant profile, where the profile typically represents the pattern or distribution of ultrasound in a plane substantially perpendicular to the main direction of propagation). Such scanning allows an ultrasound image (two or three-dimensional) to be derived across the range of tissue scanned by ultrasound beam. Note that this optically-generated scanning is usually less disruptive for a medical procedure than having to rotate or otherwise mechanically manipulate an existing instrument to perform analogous imaging.

In most cases, the positioning of the ultrasound beam will track sequentially through a set of tissue locations—such as by move the optical excitation light from one end of arrow A steadily to the other end of arrow A (as per FIG. 1A). However, in some implementations, the order of the scan through the tissue may be more complex, potentially jumping from one location to another, and then back to another, in order to populate (properly sample) the full range of scanned tissue positions.

The processing unit 200 controls the spatial and temporal pattern of illumination of the fibre bundle (including any phase offset in the modulation of different fibres, such as illustrated in FIG. 4), and also receives the modulated signal back from the optical element 155 via optical light guide 150. This information allows the processing unit 200 in effect to decode the received modulated signals, and in particular to determine a 2-D or 3-D location of various reflecting structures with respect to the distal end 103 of the medical instrument. These locations can then be displayed, as appropriate, as a 2-D or 3-D image (via projection, slicing, etc.) on monitor or display 210.

Note that for the scanning of FIGS. 2 and 3, there is a fairly immediate relationship between the elongated spatial pattern of the excitation light and the profile of the resulting ultrasound beam. However, in other embodiments, this relationship may be more distant—for example as per the implementation of FIG. 4. Accordingly, the time-varying spatial pattern applied to the proximal end of optical fibre bundle 130 is selected to provide the desired ultrasound scanning, having regard also to any optical transformation performed within the medical instrument—e.g. if there is an optical lens between the optical fibre bundle and the optically absorbing coating 135 (as discussed below), or if the optical relay performs some transformation of the light as it is conveyed from the proximal end to the distal end.

In general, an ultrasound signal is generated for instrument 10 by applying an optical signal (the excitation light) which is modulated or comprises one or more pulses (rather than a steady state optical signal). This time variation in the optical signal can take various forms, including changing the frequency/duration and/or intensity of the pulse(s) and/or modulations. For example, different pulse frequencies may penetrate to different depths of tissue—in general lower frequencies penetrate further, but provide lower spatial resolution for imaging. In addition, in some cases the pulses may be digitally coded in accordance with a known sequence (e.g. a Gold code or a Barker code) to provide improve signal detection of a reflected ultrasound signal. Other possibilities are for the excitation light to include signals such as frequency chirps, an alternating sequence with different frequency contents, and/or pulses with different rise times.

We can therefore recognise two levels of time variation with system 10. The first level relates to the form of the excitation signal provided at a given location, and is used to generate a desired (but substantially fixed) pattern of ultrasound radiation propagating into the tissue. Many existing ultrasound systems generate ultrasound in a similar manner, e.g. by applying excitation pulses electrically. The second level relates to time variations in the spatial pattern across many different locations of the excitation signal, such as the scanning illustrated in FIGS. 2 and 3, which in turn cause a beam ultrasound 171 in the tissue to be scanned through the tissue. The processing unit 200 can use knowledge about these temporal and spatial patterns of excitation light in order to derive a spatial ultrasound image of structure within tissue 300 from the received signals. For certain patterns of excitation light, the processing unit 200 may also be able to analyse the components of the received ultrasound signal to derive information on the change of phase for specific time delays between pulses, which in turn provides a mechanism to obtain Doppler measurements regarding motions within the tissue (e.g. blood flow).

The approach discussed above can be assisted by focussing the ultrasound waves 171 produced by the optically absorbing coating 135. In one respect, such focussing can help to provide additional positional (directional) information about the location of any reflecting structure, which in turn may make the final determination of position (and any resulting image) more accurate. In addition, focussing the outgoing ultrasound waves can lead to stronger reflected ultrasound waves 171B (because the propagating ultrasound waves 171A have higher peak pressures). This increase in strength of the reflected ultrasound waves generally helps with signal-to-noise ratio, and can lead to more accurate estimation of time delay, directional location, and so on.

Figure 5A:
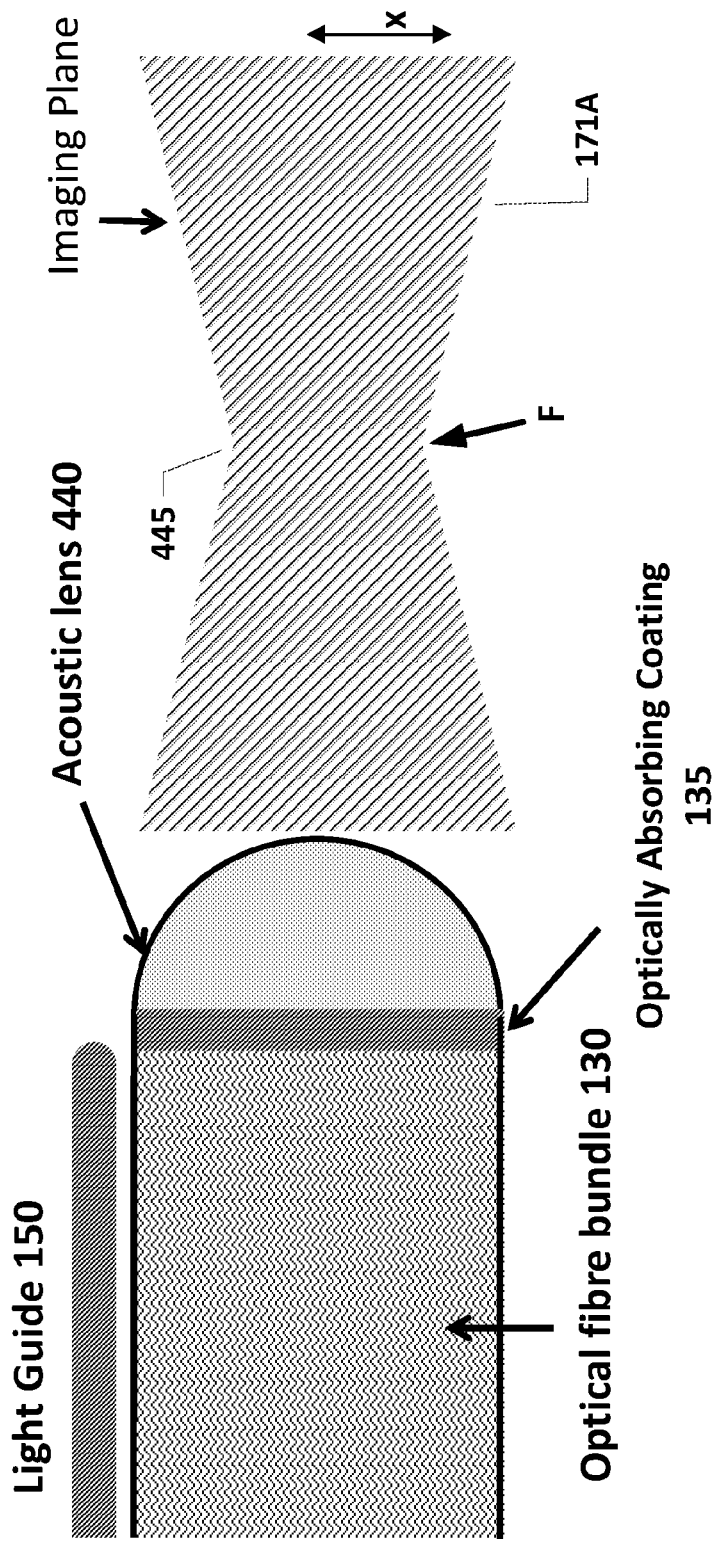
FIGS. 5A and 5B are schematic diagrams of an acoustic lens at the distal end of the optical fibre bundle of FIG. 1 in accordance with some embodiments of the invention.
Figure 5B:
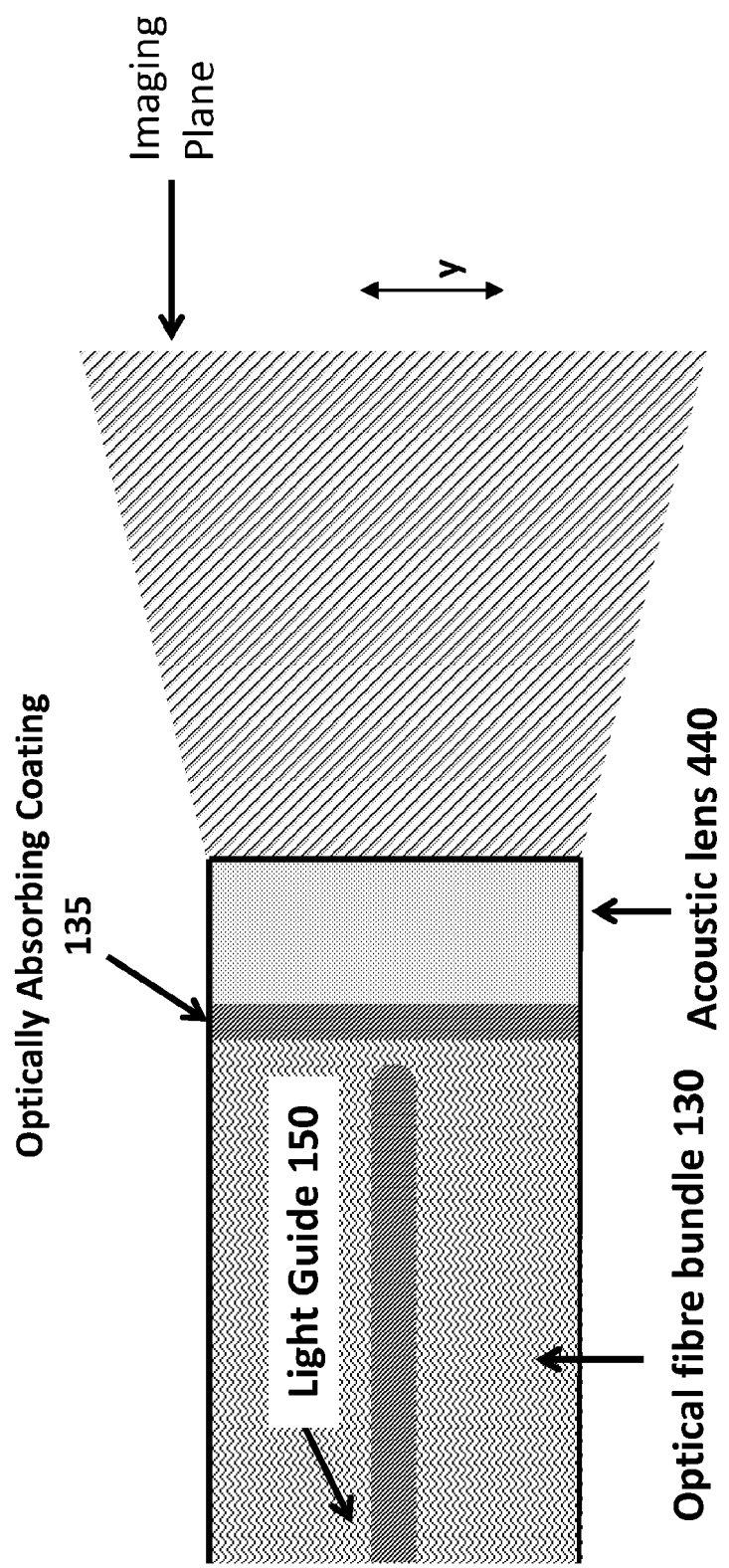

There are a number of ways and directions in which such ultrasound focussing may be achieved. For example, one possibility is to focus the ultrasound waves generated by the optically absorbing coating 135 using an acoustic lens. This is illustrated in FIG. 5, in which FIG. 5A shows a view of the X-Z plane, and FIG. 5B shows a corresponding view of the Y-Z plane. It can be seen that an acoustic lens 440 is located at the distal end 103 of the medical instrument 100, adjacent to optically absorbing coating 135 (which in turn is adjacent to the distal end of the optical fibre bundle 130). This acoustic lens has a generally cylindrical shape, with a semi-circular cross-section, where the longitudinal axis of the cylindrical shape runs parallel to the Y axis as indicated in FIG. 2.

The acoustic lens 440 acts to focus the ultrasound waves 171A produced by the optically absorbing coating 135 to a focus position as indicated by the letter F in FIG. 5A within the plane of curvature of the acoustic lens (the cylindrical axis of acoustic lens 135 runs perpendicular to this plane). The focus, also denoted by reference number 445, represents a point of constriction in the X-coordinate, i.e. a line of focus perpendicular to the main propagation direction of the ultrasound, and therefore helps to define an imaging plane which is coincident with the Y-Z plane (as shown in FIG. 5B). Accordingly, the ultrasound system is generally able to obtain a good signal from structures that fall within the imaging plane because the ultrasound waves 171 from the optically absorbing coating 135 are concentrated into this plane, and hence give stronger reflected signals 171B from any tissue structures that may be located in or close to this imaging plane. Note that in use, the medical instrument may be rotated (about axis Z) to likewise rotate the imaging plane if so desired.

Figure 6A:
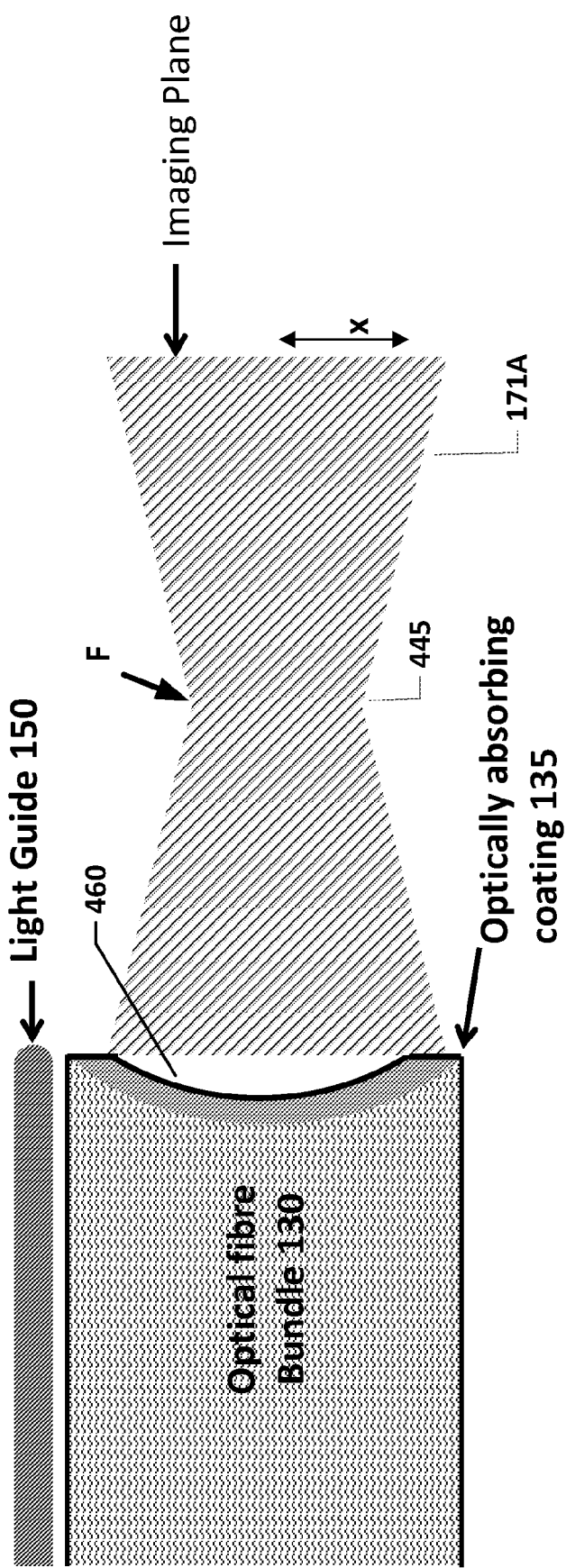
FIGS. 6A and 6B are schematic diagrams of curvature on the optically absorbing coating at the distal end of the optical fibre bundle of FIG. 1 in accordance with some embodiments of the invention.
Figure 6B:
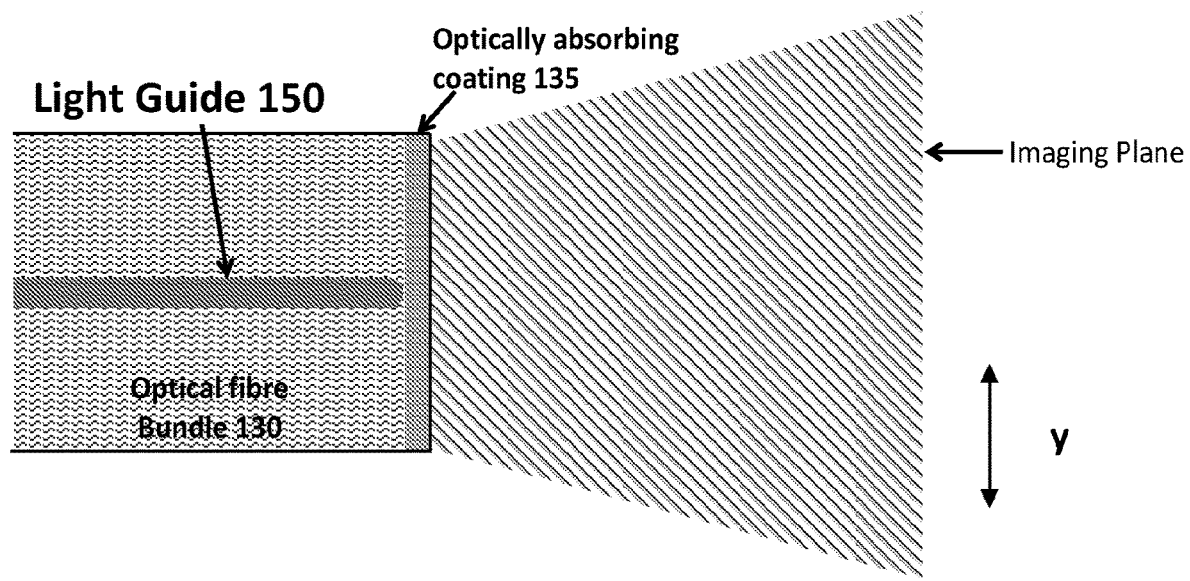

An alternative approach to produce a somewhat similar outcome is illustrated in FIG. 6 (where FIGS. 6A and 6B have the same geometry as FIGS. 5A and 5B respectively). In this example, the surface of the optical fibre bundle 130 is curved inwardly, with the plane of curvature again assumed to be located in the X-Z plane. This curvature 460 can be created by polishing an optical fibre bundle, and the optically absorbing coating 135 is located on this curved surface to produce a focus F, 445, which again provides a form of constriction in the X direction of the imaging plane of the ultrasound beam.

Other focussing techniques are also available, such as discussed above in relation to the phased array of FIG. 4. Another possibility would be to create regions R1, R2, R3, etc as concentric circles. The application of suitable timing delays to these different regions can be used to create ultrasound waves that converge (approximately) to a single point (corresponding to the centre of the rings).

In some cases, the distal end 103 may be provided with a facility to diverge (rather than focus or converge) the ultrasound radiation. This may be achieved, for example, by using a convex acoustic lens, or a convex shaping of the optical coating at the end of the fibre bundle, or any other appropriate technique. Spreading out the ultrasound beam in this manner provides a wider field of view (albeit with a potentially weaker or more diluted signal strength). In some implementations there may be an ultrasound beam which is focussed (converging) in respect of one dimension, e.g. as defined by the X-axis, and diverging in another dimension, e.g. as defined by the Y-axis.

Figure 6C:
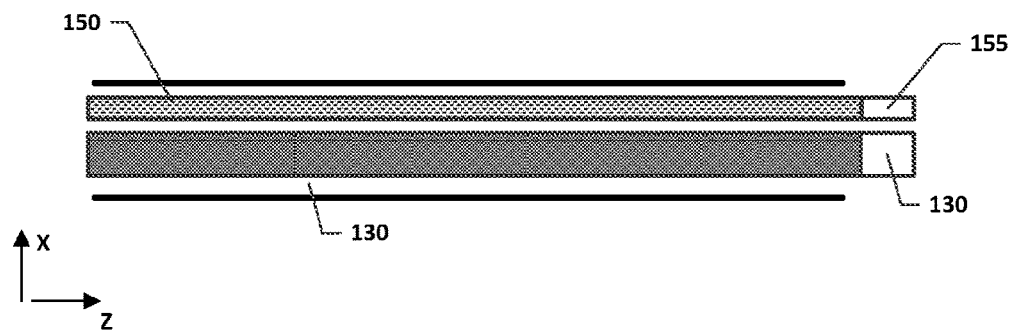
FIGS. 6C and 6D are schematic diagrams of illustrating a facility for obtaining a deflected ultrasound beam at the distal end of the optical fibre bundle of FIG. 1 in accordance with some embodiments of the invention.
Figure 6D:
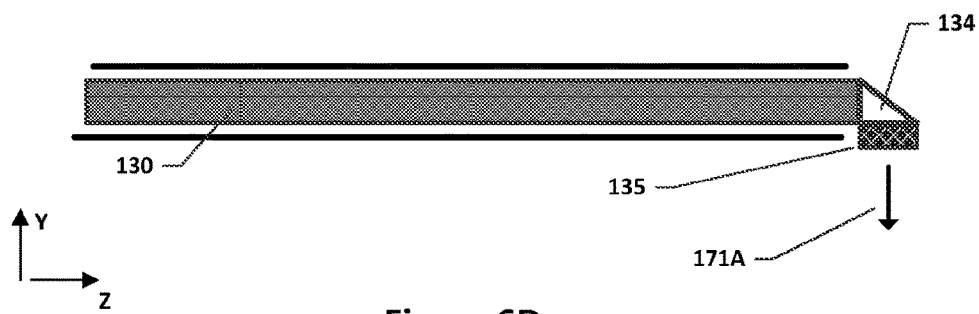

In addition to focussing (or diverging) the ultrasound beam 171A, the medical instrument may also be provided with some facility for deflecting (or reflecting) the ultrasound beam 171A. This is shown in FIGS. 6C and 6D, whereby FIG. 6C shows a simplified view of the medical instrument 100 generally analogous to that shown in FIG. 1. However, as can be seen best in FIG. 6D, a prism is inserted between the optical fibre bundle and the ultrasound absorbing coating. This prism has the effect of reflecting the excitation light by 90 degrees, so that it travels in the Y direction (rather than the Z direction). In addition, the optical absorbing coating 135 is now arranged in the X-Z plane (rather than the X-Y plane), hence the excitation light and the resulting ultrasound beam 171A now propagates parallel to the Y axis. This ability to deflect or alter the angle of the ultrasound beam (whether by 90 degrees or by some other suitable angle) may be useful according to the location of a tissue structure 310 to be observed compared with the insertion direction of the medical instrument 100 (which may be subject to anatomical constraints, etc).

Although the implementation performs a deflection of the excitation light, in other cases the excitation light may pass directly into the optical absorbing coating 135, hence the generated ultrasound beam 171A is initially parallel to the Z axis. An appropriate deflector, e.g. comprising one or more ultrasound reflectors, lenses, etc) can then be used to deflect the ultrasound beam 171A away from the Z axis. Similarly, an appropriate deflector may also be used to deflect an incoming ultrasound beam 171B onto the optical element 155, depending upon the geometry of the medical instrument 100.

In some embodiments, the optically absorbing coating 135 comprises wavelength-selective optical absorbers that are substantially absorbing at a first wavelength range and substantially transmissive at a second wavelength range. These wavelength-selective optical absorbers could include, for instance, gold nanoparticles such as gold nanorods. To generate ultrasound, excitation light in the first wavelength range is used, which is converted by the optical absorbing coating 135 into ultrasound waves 171 that propagate into the tissue. However, if the optical fibre bundle is also used to transmit light falling into the second wavelength range, then a substantial fraction of this light in the second wavelength range will propagate through the optically absorbing coating 135 into tissue 300. This light in the second wavelength range may be used, for example, to generate ultrasound waves in the tissue itself via the photoacoustic effect, and the resulting ultrasound can then be received by the optical element 155 and optical light guide 150. It can also be used, for example, to deliver light into tissue for ablation. The light in the second wavelength range that propagates into tissue can also be used to generate microscopic images, for instance, for confocal laser scanning endomicroscopy, and/or optical endoscopic images. This microscopic imaging may involve having an optical lens positioned proximal or distal to the optically absorbing coating 125 (in the latter case, the optical lens should be constructed from a material that is at least partially transparent to ultrasound waves, such as polydimethylsiloxane (PDMS).

Although FIGS. 5 and 6 show the optically absorbing coating 135 at the distal end of the fibre bundle being located directly on the fibre bundle 130, in some cases there may be one or more intervening components. For example, one possibility is that some lens or other optical system is positioned between the fibre bundle itself and the optically absorbing coating 135. Such an optical system might be used, for example, to diverge or converge the spatial pattern of excitation light emerging from the optical fibre bundle onto the optically absorbing coating 135 in order to help control better the resulting ultrasound beam.

Figure 7:
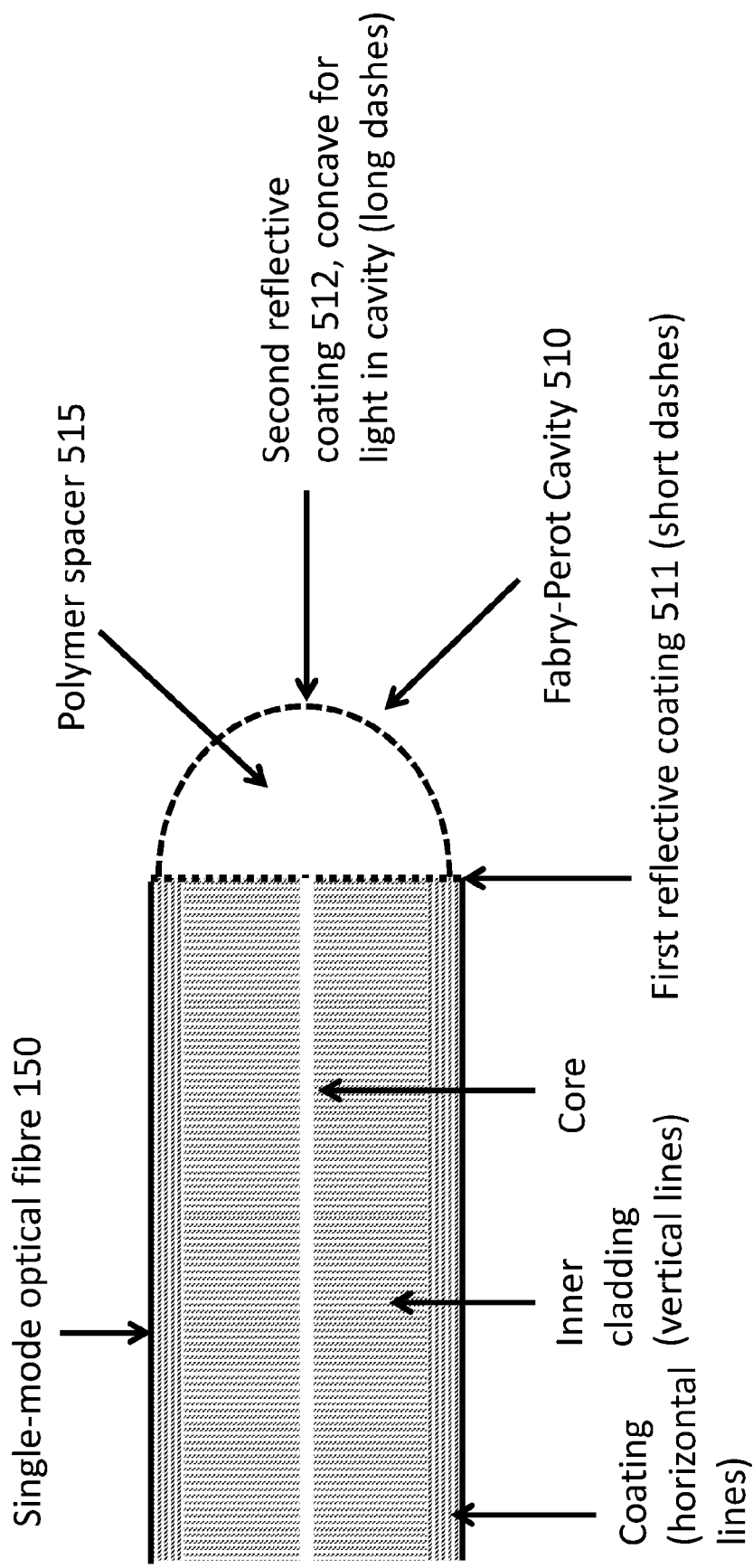
FIG. 7 is a schematic diagram of a Fabry-Pérot cavity at the distal end of the optical light guide of FIG. 1 in accordance with some embodiments of the invention.

As mentioned above, the optical element 155 may comprise an ultrasound receiver that is positioned adjacent to the distal end of an optical light guide 150. As shown in FIG. 7, in some embodiments the ultrasound receiver is implemented using a Fabry-Pérot cavity 510, while the optical light guide is a single mode optical fibre 150 (with the Fabry-Pérot cavity at the distal end). The Fabry-Pérot cavity comprises first and second dielectric reflective layers 511, 512, that are separated by a spacer element 515, with the first reflective layer 511 positioned at the distal end of the optical fibre and the second reflective layer 512 positioned at the distal end of the spacer element. The spacer element 515 shown in FIG. 7 is convex. This helps to increase the number of reflections within the Fabry-Pérot cavity, which in turn improves the sensitivity. However, in other implementations the spacer element 515 and the second reflective surface 512 of the spacer may be planar.

The medical instrument 100 may be provided with an acoustic lens (analogous to the acoustic lens of FIG. 5). Such an acoustic lens can help to focus incoming ultrasound waves 171B onto the optical element, thereby providing a stronger signal for detection and transducing by the optical element. In addition, the medical instrument 100 may be provided with multiple ultrasound receivers, which can be positioned in any suitable configuration with respect to the optical fibre bundle 130. The presence of multiple ultrasound receivers can also help to provide information regarding the direction of tissue structures that are reflecting ultrasound waves (based on slight differences in times of receipt of a given reflection signal at respective hydrophones). Other arrangements are possible, for example, there may be multiple optical fibre bundles 130 for transmitting the excitation light which are arranged around the optical light guide 150 used for conveying the received signal back to the processing unit 200.

Other options for implementing the optical light guide 150 are a multimode fibre or a fibre bundle. These systems potentially allow for different spatial patterns of the interrogation light supplied to the optical element, and hence could modify the sensitivity of this optical element, for example with respect to different spatial positions and different angles. One such possible implementation has an optical fibre bundle as the optical light guide 150 which illuminates (interrogates) one or more Fabry-Pérot cavities as the optical element. This illumination may locate one or more additional optical devices between the optical light guide 150 and the ultrasound receiver 155, such as a GRIN (gradient index) lens.

In some implementations, the Fabry-Pérot cavity used for optical element 155 is wavelength-selective, i.e. it is highly reflective at optical wavelengths in a first range used by the interrogation light to receive ultrasound, and highly transmissive to light with wavelengths in a second range. Accordingly, pulsed or modulated light with a wavelength in the second range can be transmitted by the processing unit (or any other suitable device) from the proximal end 102 of the medical instrument 100 to the distal end 103 along the optical light guide 150, and then pass through the Fabry-Pérot cavity (optical element 155) into tissue 300. One motivation for transmitting light into tissue via optical light guide 150 would be to produce ultrasound waves via the photoacoustic effect. Another possibility would be for the light in the second wavelength range to provide illumination to help perform microscopy, such as laser-scanning confocal microscopy, or endoscopy.

In certain embodiments, the optical light guide 150 has a distal section which is relatively short and is mechanically separate from a proximal section. In use, the distal section is fixed to the proximal section. Such an implementation allows the proximal section to be re-sterilised after it has been used in a clinical procedure (in contrast, the distal section may not be re-sterilisable due to potential damage to the optically absorbing coating).

The medical instrument may also include a facility for providing illumination onto tissue ahead of the probe. One possibility is for this illumination is to create a pattern of excitation light through a wavelength-selective optically absorbing coating that is substantially confined to a small number of fibres within the fibre bundle 130, and to raster-scan this pattern in the x- and y-dimensions. This raster scanning can be performed, for instance, with a resonant galvanometer mirror in the x-dimension, and a non-resonant galvanometer mirror in the y-dimension. The excitation light can be used to generate ultrasound from spatially localised regions in the tissue 300 with the photoacoustic effect, and the received ultrasound signals can be processed to generate a photoacoustic microscopy image. It can be appreciated that different scanning patterns, such as circular scanning patterns, can also be used, and that different wavelengths of excitation light can be provided to tissue to obtain information about different tissue chromophores. It can also be appreciated that different spatial patterns of excitation light, such as spatial patterns that span a significant fraction of the fibres within the fibre bundle 130, and spatial patterns that are substantially orthogonal to each other with which to perform compressed sensing, could be used. Photoacoustic microscopy images can be superimposed with ultrasound images that are created with excitation light that is absorbed by the optically absorbing coating, on the same display. In a preferred embodiment, illumination of tissue is performed at different times than illumination of tissue.

A specific set of clinical applications for which optical ultrasound is well suited involve transseptal puncture, which involves crossing a tissue division between chambers within the heart, for example from the right atrium to the left atrium. This crossing should be performed at a thin section of tissue, such as the intra-atrial septum that lies between the two atria (unless it is not present, which occurs occasionally). A common clinical procedure in which transseptal puncture is performed is catheter ablation of the left atrium to treat a condition called atrial fibrillation. A typical commercial transseptal puncture needle has a length in the range 70-100 cm (with a shorter length for pediatric procedures), and the inner diameter of the cannula at the distal end of the needle is of the order of 0.5 mm. An important aspect of such procedures involving transseptal puncture is the (simultaneous) measurement of cyclic cardiac pressure waveforms.

Although the integration of optical transmitters and receivers into a needle has been proposed in existing work, these proposals are generally unsuitable for transseptal puncture. For example, Acquafresca et al. have presented a diagram for multiple transmitters and one receiver (Acquafresca, 2003), but their design would be difficult to implement in transseptal puncture due to the small cross-sectional dimensions of the transseptal puncture needle. Similarly, the PhD dissertation of Luca Belsito (Belsito, 2011) shows a device in which an optical transmitter and receiver are mounted on distinct optical fibres and then inserted into the lumen of a syringe needle.

The medical instrument 100 (and associated overall system 10) shown in FIG. 1 can be configured for performing a transseptal puncture. The medical instrument 100 incorporates an ultrasound sensing probe having at least one optical fibre (such as optical fibre bundle 130) for generating ultrasound, and an optical fibre (such as optical light guide 150) for receiving ultrasound. The optical fibres may be integrated into a stylet that can be removed from the transseptal needle cannula, or they may be integrated into the transseptal puncture needle.

Figure 8:
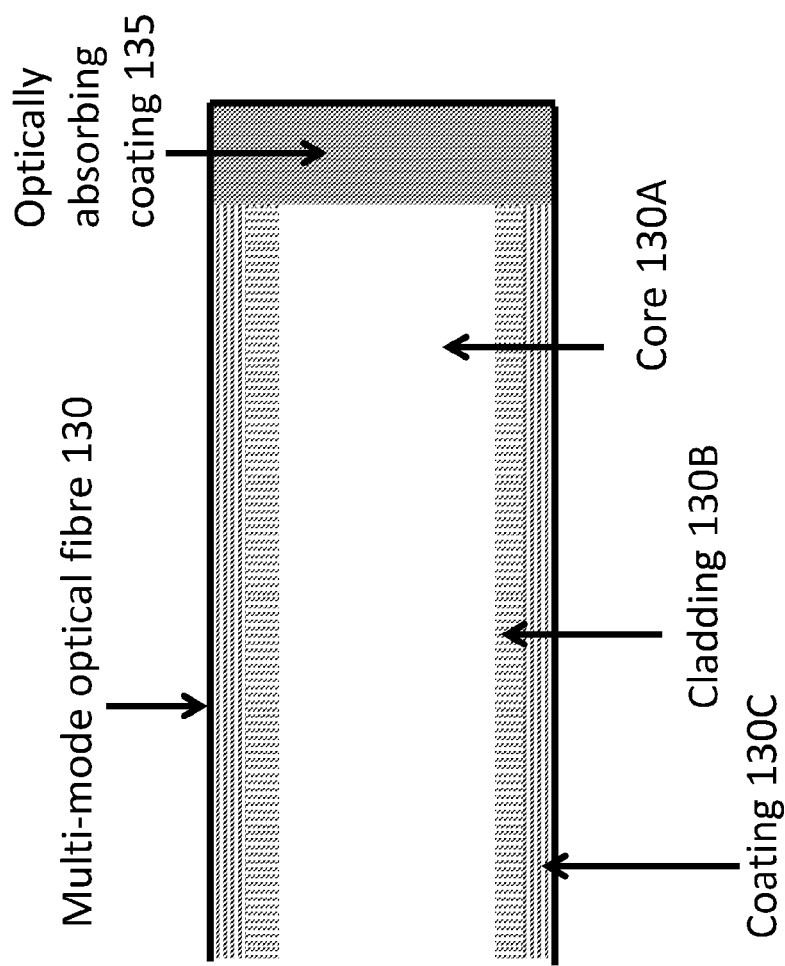
FIG. 8 is a schematic diagram of the distal end of an optical fibre used to generate ultrasound in accordance with some embodiments of the invention.

As illustrated in FIG. 1, the optical fibre(s) 130 for generating ultrasound are provided with an optically absorbing coating 135 at the distal end 103. In an example implementation, the optical fibre 130 may comprise a multi-mode fibre 130 as shown in FIG. 8, with a silica core 130A, a silica cladding 130B, and an outer coating 130C. In some implementations, the optical fibre(s) 130 has a core with a diameter less than 300 microns. For example, diameter of the core, the cladding, and any outer coatings may be 200, 210, and 235 µm, respectively. In other implementations, the optical fibre 130 used for generating ultrasound in the transseptal puncture needle may comprise a single mode fibre 130.

Light transmitted along the optical fibre(s) 130 is incident on the optically absorbing coating 135. Several optically absorbing coatings for generating ultrasound are known, such as composites comprising PDMS and carbon nanotubes.

The optical fibre 150 for receiving ultrasound may be a single mode optical fibre. Such a single-mode optical fibre may have a cladding diameter of 80 µm and a coating diameter of 175 µm. The optical fibre 150 is provided with an ultrasound-sensitive element 155 (hydrophone) at the distal end 130, which has optical characteristics that change in the presence of ultrasound waves. One implementation for this ultrasound-sensitive element is a Fabry-Pérot cavity that is positioned at the distal end of the fibre, for example, as illustrated in FIG. 7. Such a Fabry-Pérot cavity 510 may be formed with a first reflective layer 511 on the distal end 103 of the optical fibre 150, an optically transparent spacer 515, and a second reflective layer 512 on the distal end of the optically transparent spacer. The reflective surfaces may be gold coatings or dielectric coatings (for example). As shown in FIG. 7, the distal end of the optically transparent spacer 515 and the second reflective surface 512 of the cavity may be concave for light within the cavity. This concave surface can be created, for example by dip coating using an optical epoxy, and helps to increase sensitivity.

The processing unit 200 (or sensing console) includes (or is used in conjunction with) a light source that delivers light to the optical fibre(s) 130 for generating ultrasound. This may be achieved, for example, using a simplification of the apparatus shown in FIG. 1A (e.g. there is no need for mirror 196 to perform scanning in this configuration). The light source provides pulses of light with a pulse width (FWHM) typically less than 50 ns in duration. Additionally, the light source may be able to provide light in which the intensity is modulated over a time period longer than such a typical pulse width—for example, for a frequency chirp. A further possibility is that a sequence of pulses is produced based on a digital code, such as a Barker code or a Gold code, where such a sequence has low autocorrelation properties. Such a sequence supports accurate measurement of the timing delay of a reflected signal (such as 171B in FIG. 1), since cross-correlating a received signal with the known outgoing signed should yield a sharp correlation peak at the relevant timing delay (which in turn indicates the ultrasound propagation time to and back from any reflecting structure 310). The use of such a sequence also helps to detect the reflected signal in the presence of noise, even if the reflected signal is rather weak.

The light source may also provide a sequence of pulses or intensity modulations that generate ultrasound waves with substantially different ultrasound frequency spectra, for example, so as to alternate between lower frequency and higher frequency ultrasound waves. It will be appreciated that lower frequency ultrasound waves tend to result in lower spatial resolution image, but can penetrate greater depths into tissue 300, than higher frequency ultrasound waves. Accordingly, the use of lower frequency and higher frequency ultrasound waves can help to produce a better quality and more extensive ultrasound image.

The system 10 can also process the received ultrasound signal to derive a Doppler contrast by comparing the phases of the signals from consecutive ultrasound scans. For example, to obtain Doppler contrast, two or more modulations of light can be performed in rapid succession (typically a few microseconds or less), followed by a longer time delay (e.g. 10 ms). Note that the Doppler contrast may be obtained using modulations (e.g. chirped signals) that are distinct from those used for ultrasound imaging (e.g. pulses), with the Doppler contrast signals and the imaging signals provided in alternating or interleaved fashion. A Doppler signal produced in this fashion may be superimposed on the display ultrasound image, for example, an M-mode image.

Figure 9:
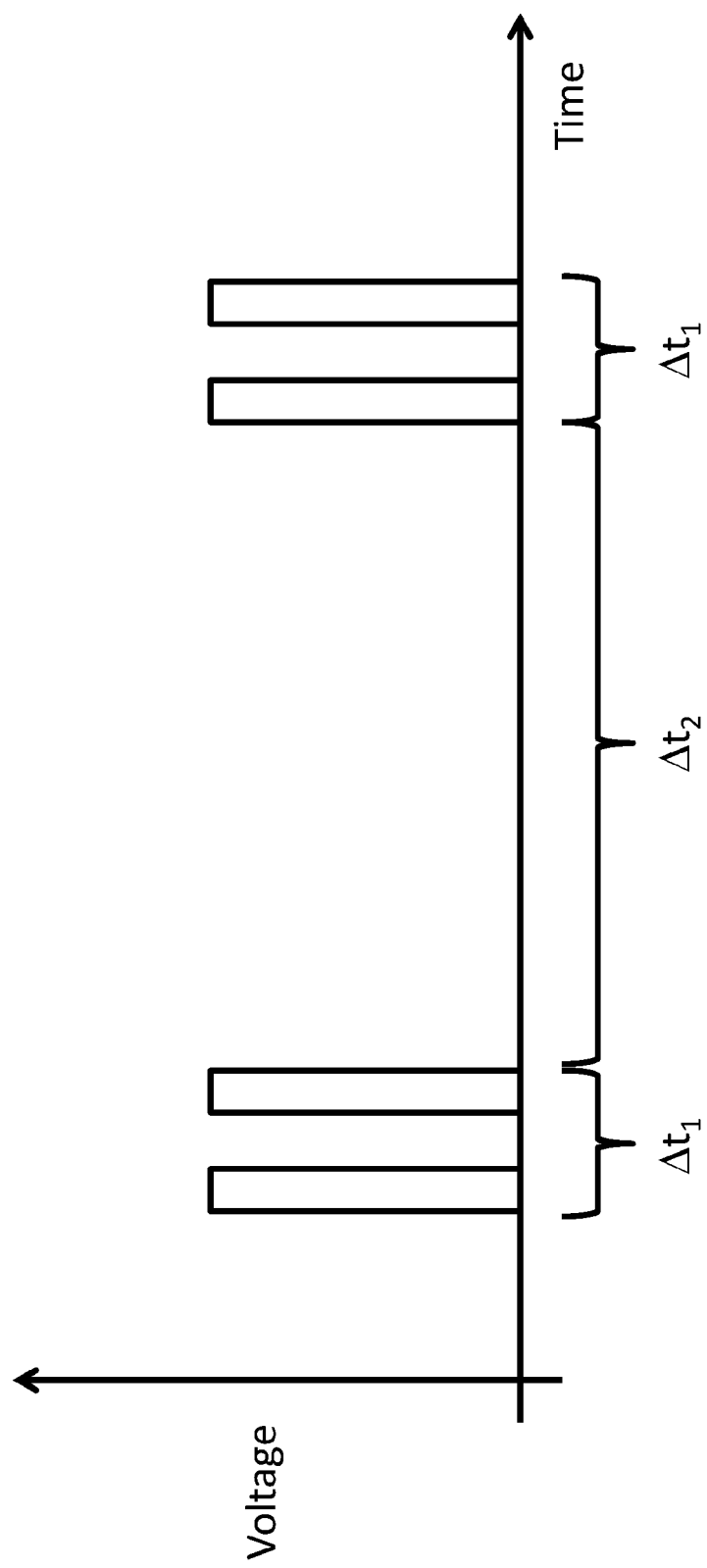
FIG. 9 is a schematic diagram of a sequence of pulses used to generate ultrasound signals in accordance with some embodiments of the invention.

FIG. 9 is an example of a pulse sequence that may be provided by the processing unit 200 and subsequently converted into an ultrasound signal into tissue 300 to obtain Doppler contrast. This pulse sequence comprises pulses with alternate time spacings of $\Delta t_1$ and $\Delta t_2$. This can be regarded as two simultaneous pulse sequences, one with a period of $\Delta t_1$, the other with a period of $\Delta t_1 + \Delta t_2$ (where each pulse in the latter sequence can be regarded as formed from two successive pulses separated by $\Delta t_1$). The pulse sequence shown in FIG. 9 is able to detect movement, since if a source of reflection 310 is moving towards or away from the ultrasound probe, this will impact the delay time for reflections of the returning ultrasound waves). For example, in accordance with the Doppler effect, if the source of reflection is moving towards the probe, then the pulse reflections as received at the ultrasound probe will have a smaller spacing (higher frequency) than the originally transmitted pulse sequence or a different phase. It will be appreciated that a relatively short pulse spacing of $\Delta t_1$ is good for detecting higher velocity movement, especially if this is subject to change, whereas the longer pulse spacing of $\Delta t_2$ is good for detecting lower velocity movement with respect to the ultrasound probe.

The processing unit 200 (sensing console) also comprises (or is used in conjunction with) a light source that delivers interrogation light to the hydrophone (the ultrasound-sensitive element 155) via the optical fibre 150 for receiving ultrasound. For devices having a Fabry-Pérot cavity 510 as the ultrasound-sensitive element 155, a portion of the light from this source reflects from the Fabry-Pérot cavity 510 and is received by electro-optical coupler 145, which may be implemented (for example) by a photodetector.

In some implementations, the interrogation light source may be continuously tuned to different wavelengths to optimise the sensitivity of the hydrophone to ultrasound. As the wavelength of the light source is varied, the DC component of the signal received at the photodetector is recorded, so as to measure the rate of change of the transfer function with respect to wavelength (as described by Morris, 2009). Additionally, the light source can be tuned based on information from a temperature sensor. The timing with which the laser is tuned can be performed synchronously with the light pulses or intensity modulations that are used to generate ultrasound. The high frequency components of the signal from the photodetector (typically greater than 500 kHz and less than 75 MHz) are recorded and used to generate a visual display.

The signal received by the electro-optical coupler 145 (such as a photodetector) from the optical fibre 150 that receives ultrasound can be processed using appropriate known methods, such as a band-pass filter, a Hilbert transform, and logarithmic compression of the absolute value of the output of the Hilbert transform. The output of individual depth scans may be provided by the processing unit 200 to display 210, where they can be displayed, for example, as an M-mode image, with depth as the vertical axis and time as the horizontal axis.

In some implementations, information about the position of the needle tip (i.e. the distal end 103 of the medical instrument 100) is determined from a second imaging or sensing system. For instance, one or more electromagnetic (EM) trackers may be placed within the transseptal puncture needle or instruments containing the transseptal puncture needle, and signals generated from these EM trackers can then be processed to obtain information about the position of the needle tip. This position information can contribute to the generation of an ultrasound image by allowing individual scans to be displayed (or processed) according to the spatial position in which they were acquired. Note that the second ultrasound imaging system may be internal or external; for example, it might be an ultrasound system positioned in the oesophagus or even inside the heart.

Figure 10:
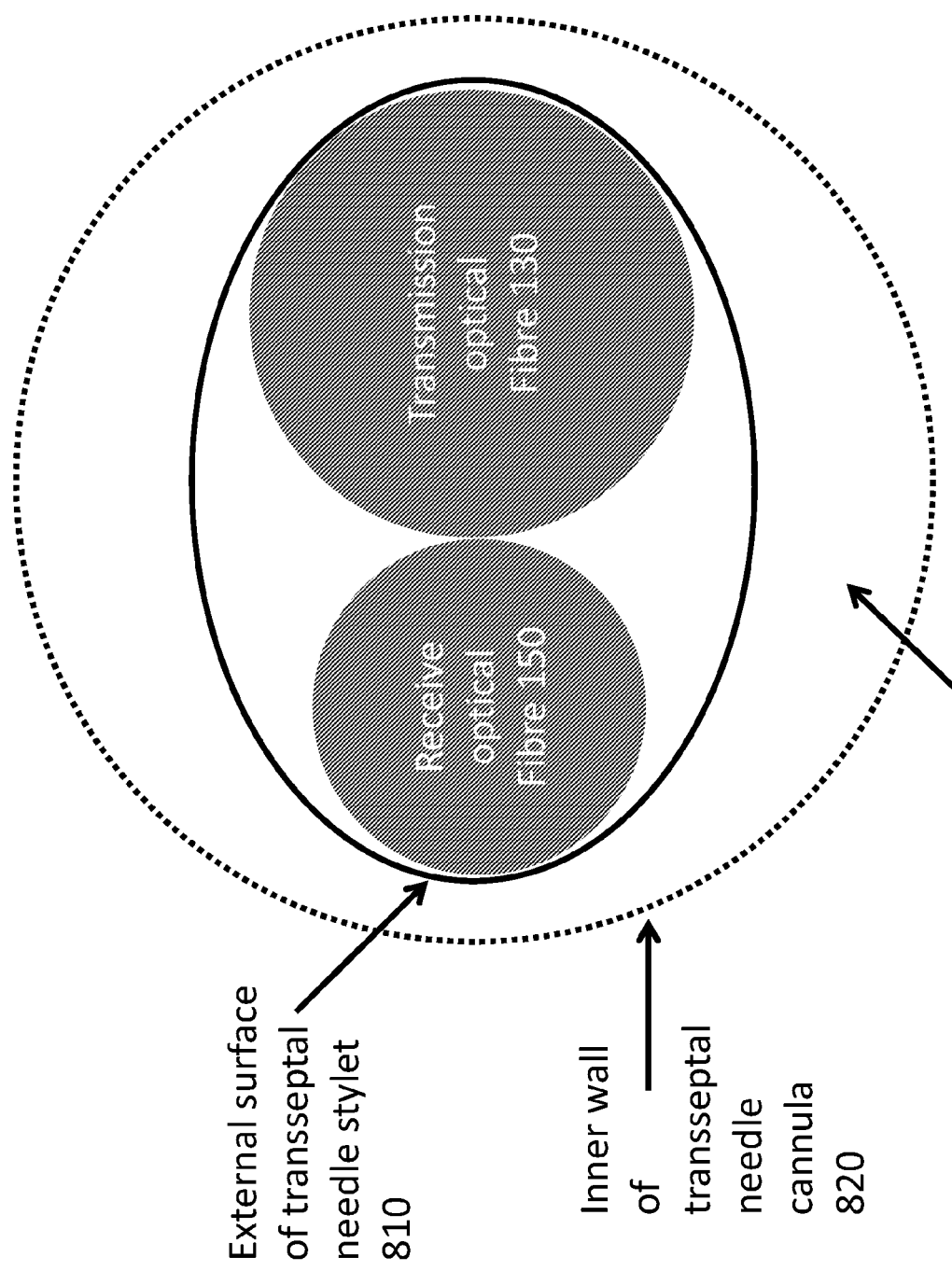
FIG. 10 is a schematic cross-section through a transseptal puncture needle in accordance with some embodiments of the invention.

For transseptal puncture, the device 100 supports the measurement of systolic blood pressure waveforms (unlike existing devices, which do not support measurement of pressure waveforms from within the chamber or vessel within which a device is placed). In some implementations, there is space surrounding the optical fibres 130, 150 to allow a fluid column (e.g. using saline) to be established along the length of the needle. This space can be provided in different ways. For example, it may be provided by a dedicated tubular structure, or in the region surrounding the stylet within the cannula. This latter option is illustrated in FIG. 10, which presents a transverse cross-section through the medical instrument 100 (i.e. in a plane perpendicular to the longitudinal direction as represented by the Z-axis. As shown in FIG. 10, the transmission optical fibre 130 and a fibre optic ultrasound receiver are both contained within a wall 810 of a transseptal needle stylet, which in turn is contained within a transseptal needle cannula 820. There is a lumen or space 830 inside the needle cannula (but outside the needle stylet). A fluid column exists within this space 830, thereby allowing the pressure at the distal end 103 of the ultrasound probe 100 to be measured at the proximal end 102. For example, the proximal end of the 102 may be linked to a manometer in order to measure and record the pressure at the distal end 103 of the instrument.

Figure 11A:
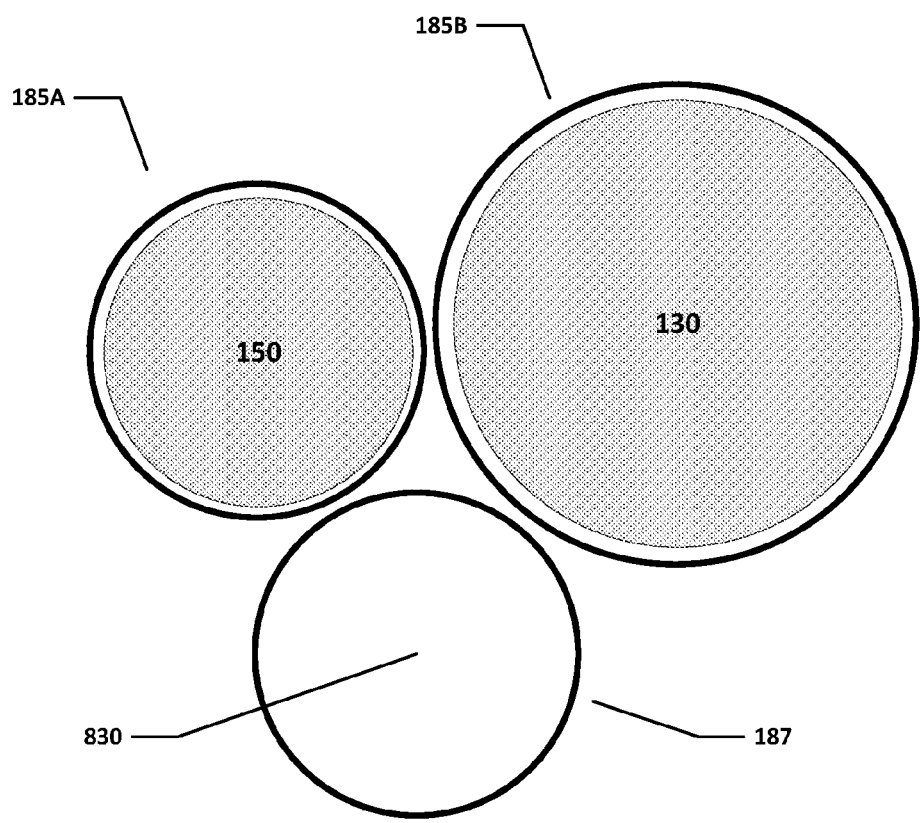
FIGS. 11A and 11B are schematic cross-sections through a transseptal puncture needle in accordance with some other embodiments of the invention.
Figure 11B:
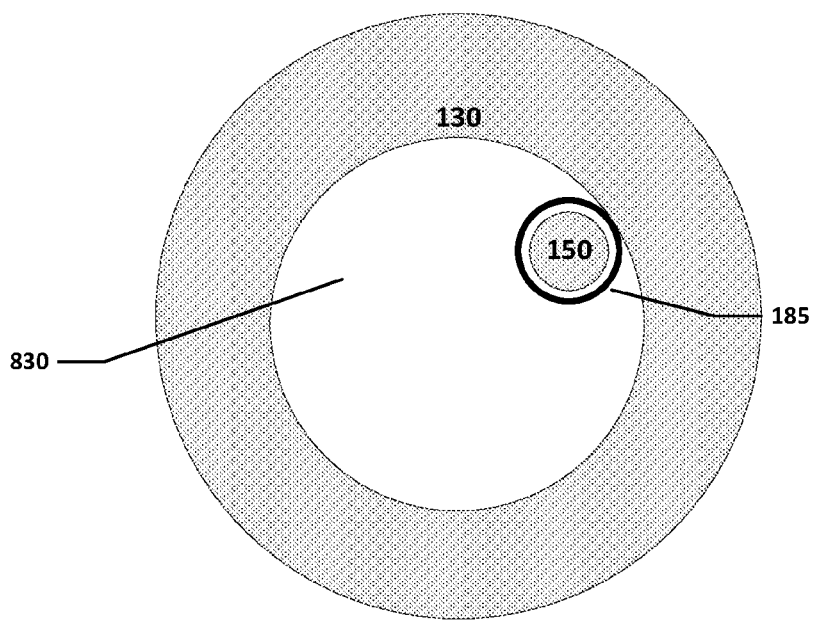

FIGS. 11A and 11B illustrate two further implementations of the internal arrangement of the transseptal needle. FIG. 11A is based on the geometry discussed above in relation to FIG. 1C, but supplemented by an additional tube or channel 187 to provide space 830 for fluid pressure transfer from the distal end to the proximal end. Similarly, FIG. 11B is based on the geometry discussed above in relation to FIG. 1F, except that the optical light guide 150 and its associated hypotube 185 occupy a smaller proportion of the internal space of the optical fibre bundle 130, with the remaining space 830 then being available for the fluid column to support pressure measurement. It will be appreciated that FIGS. 11A and 11B are provided by way of example only, and the skilled person will be aware of many further possible implementations.

Figure 12:
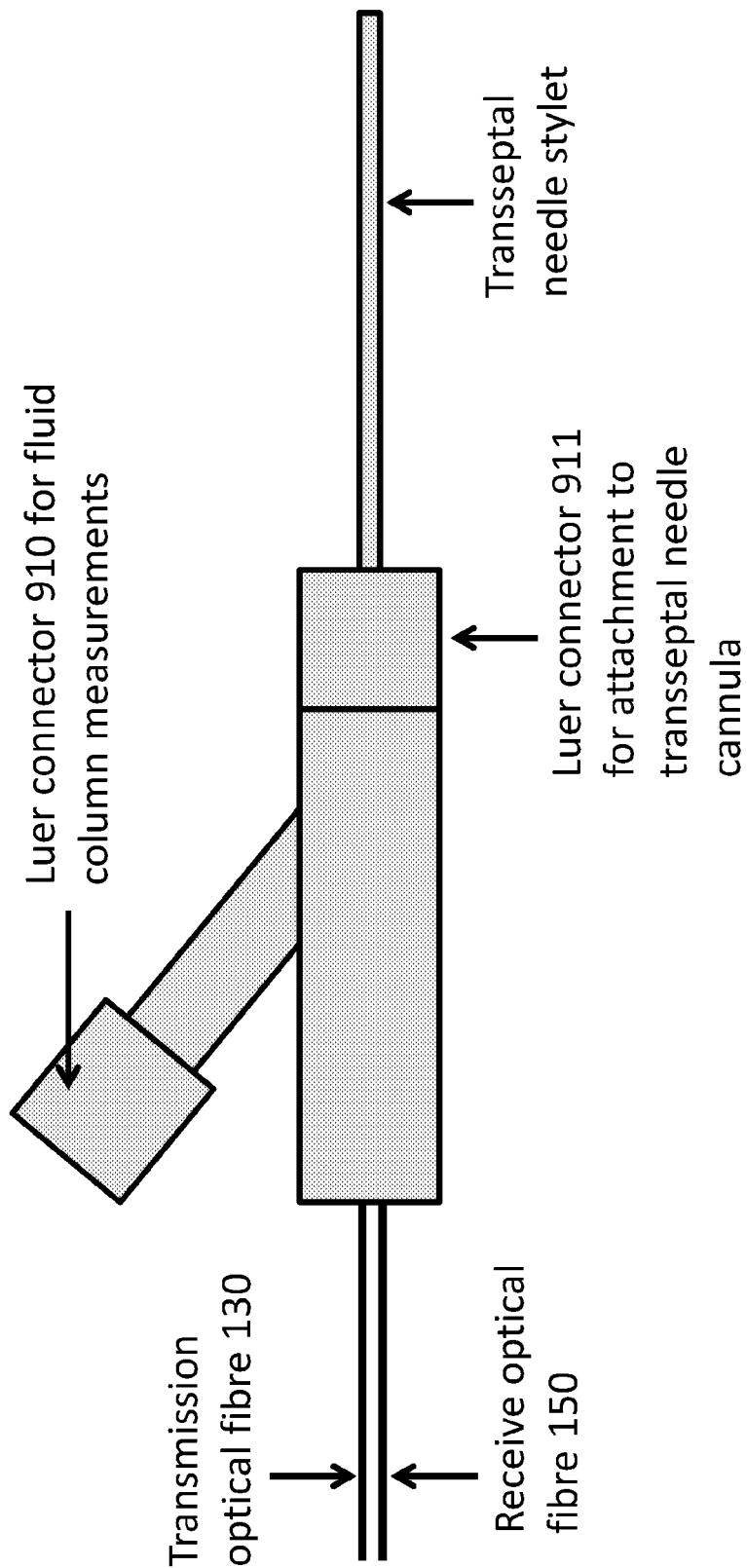
FIG. 12 is a schematic diagram of a luer connector at the proximal end of a transseptal puncture needle in accordance with some embodiments of the invention.

In some implementations, the connection of the medical instrument 100 to a manometer may be formed by means of a side-arm fitting with a luer connector. This is illustrated in FIG. 12, in which a luer connector 911 is provided for attachment to a transseptal needle cannula (not shown), which is to contain the transseptal needle stylet. The other end of the luer connector 911 receives the transmission optical fibre(s) 130 and the fibre optic ultrasound receiver 150—this is where they enter the medical instrument 100, for example, the transseptal needle stylet. This attachment device further includes an additional luer connector 910. This provides a fluid connection path from within the medical instrument, and can be used to attach a manometer or similar device for measuring pressure. In other implementations, the systolic blood pressure waveforms is measured using signals from the fibre optic ultrasound receiver 150 (instead of or in additional to those measurements obtained by using a fluid column). Such signals may be processed to obtain measurements of systolic waveforms. In particular, low frequency variations in the reflected signal that are below the usual frequency range of ultrasound (i.e. typically <1 kHz) can be processed to reveal systolic pressure waveforms (so long as the temperature is stable).

The signal received by the fibre optic ultrasound receiver 150 can be used to trigger ultrasound pulses via optical fibre(s) 130. For example, the received signal may change in the presence of ultrasound waves from a distinct (separate) ultrasound imaging system, such as an intracardiac echocoardiography (ICE) catheter, or from a transoesophageal ultrasound (TOE) imaging probe. These changes of signal may be used to trigger transmissions of ultrasound pulses using the optical fibre(s) 130, which may, in turn, be detected by the distinct ultrasound imaging system; they present as hyperechoic regions of an ultrasound image. By modulating the triggering, blinking hyperechoic regions corresponding to the position of the distal end of the ultrasound generation optical fibre(s) can be created. In this way, the triggered transmissions can be useful to localise the distal end 103 of the transseptal puncture probe or needle in the ultrasound images. The changes of signal originating from a distinct ultrasound imaging system can be differentiated from those originating from reflections of ultrasound waves generated by the transseptal puncture imaging probe due to their timing, their frequency content, and their repetition rate. The modulations of the light used to generate ultrasound can be chosen based on the detected frequency content of the detected ultrasound pulses.

Figure 13:
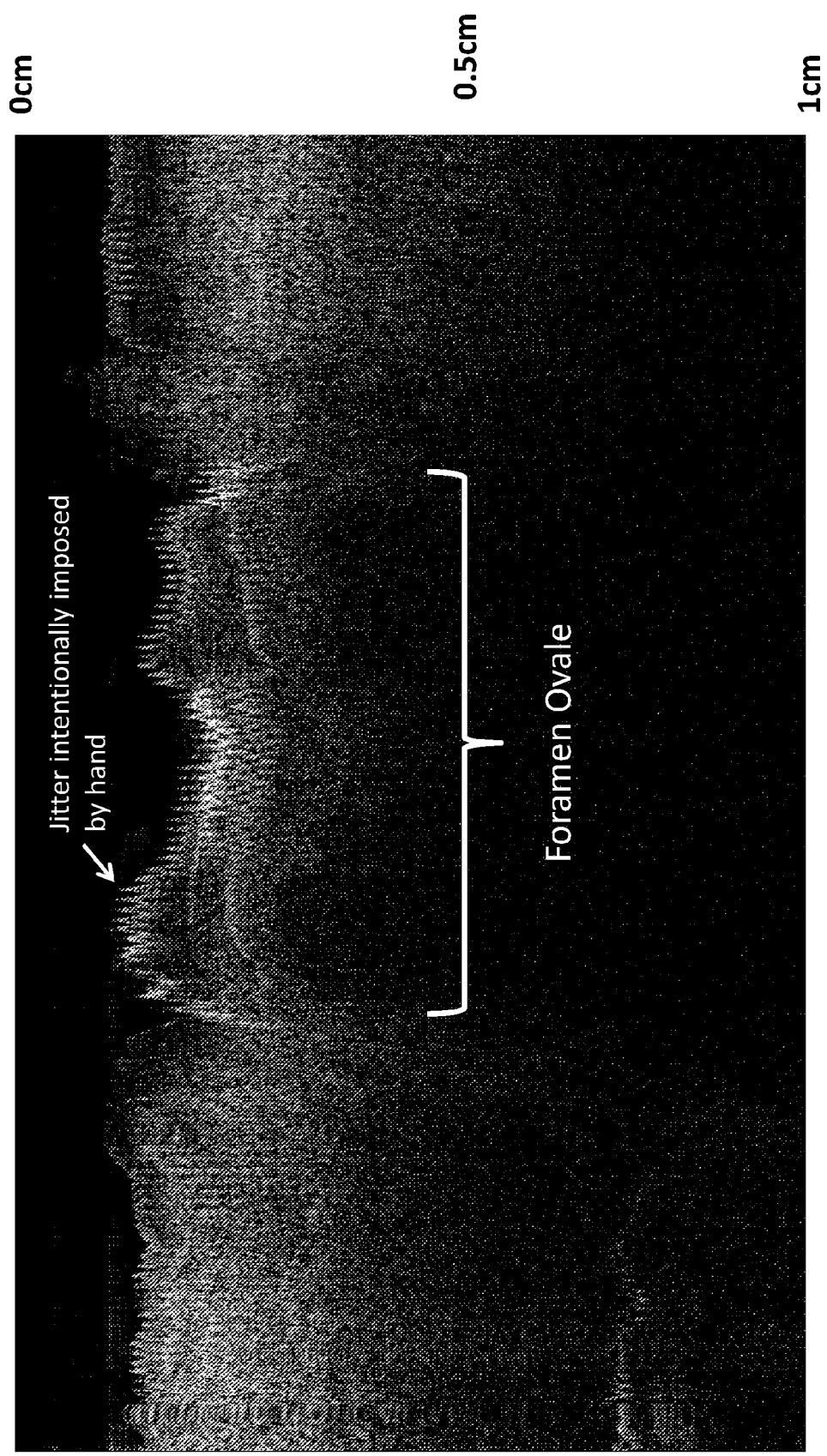
FIG. 13 is a diagram showing an ultrasound signal produced using a transseptal puncture needle in accordance with some embodiments of the invention.

FIG. 13 illustrates an ultrasound scan signal obtained using an ultrasound probe located in a transseptal puncture needle in an experimental simulation in accordance with some embodiments of the invention. In particular, FIG. 13 shows a scan signal where height on the page corresponds to depth into tissue (i.e. distance from ultrasound probe) while the direction of scan is sideways across the page. A jitter was imposed by hand on the ultrasound probe to help distinguish the received signal from noise. The ultrasound signal shown in FIG. 13 includes a clear depiction of the foramen ovale. It will be appreciated that the ability to identify such anatomical (cardiac) features is very important for clinical applications involving the use of a transseptal puncture needle.

The medical instrument 100 may further include an optical light guide for providing light to tissue surrounding the distal end of the transseptal puncture needle. The provided light may be used, for example, to obtain measurements of the optical properties of the tissue, to generate ultrasound from optically absorbing structures in the tissue via the photoacoustic effect, or to ablate tissue. In some implementations, the optical relay (fibre bundle 130) may be used as the optical light guide for providing light to tissue surrounding the distal end of the transseptal puncture needle, and the optically absorbing coating 135 is wavelength-selective so that as to be substantially transmissive to the light provided to the tissue. Another possibility is that the optical light guide (optical fibre 150) is used as the optical light guide for providing light to tissue surrounding the distal end of the transseptal puncture needle. In this case, the ultrasound-sensitive element 155 may be wavelength-selective.

The above embodiments rely on various processing, such as analysing the received signals to determination a position of the medical instrument, which may be performed by specialised hardware, by general purpose hardware running appropriate computer code, or by some combination of the two. For example, the general purpose hardware may comprise a personal computer, a computer workstation, etc. The computer code may comprise computer program instructions that are executed by one or more processors to perform the desired operations. The one or more processors may be located in or integrated into special purpose apparatus, such as an ultrasound system. The one or more processors may comprise digital signal processors, graphics processing units, central processing units, or any other suitable device. The computer program code is generally stored in a non-transitory medium such as an optical disk, flash memory (ROM), or hard drive, and then loaded into random access memory (RAM) prior to access by the one or more processors for execution.

In conclusion, the skilled person will be aware of various modifications that can be made to the above embodiments to reflect the particular circumstances of any given implementation. Moreover, the skilled person will be aware that features from different embodiments can be combined as appropriate in any given implementation. Accordingly, the scope of the present invention is defined by the appended claims and their equivalents.

REFERENCES

Acquafresca A, Biagi E, Masotti L, Menichelli D (2003) Toward virtual biopsy through an all fiber optic ultrasonic miniaturized transducer: A proposal. IEEE Trans Ultrason Ferroelectr Freq Control 50:1325-35.
Ashkenazi S, Chao C, O'Donnell M (2004) Ultrasound detection using polymer microring optical resonator. Appl Phys Lett 85:5418-5420. doi: 10.1063/1.1829775
Belsito L (2011) Design and Fabrication of MOMS-Based Ultrasonic Probes for Minimally Invasive Endoscopic Applications, PhD dissertation, University of Bologna
Biagi E, Margheri F, Menichelli D (2001) Efficient Laser-Ultrasound Generation by Using Heavily Absorbing Films as Targets. IEEE Trans. Ultrason. Ferroelectr. Freq. Control. pp 1669-1680
Biagi E, Cerbai S, Masotti L, et al. (2010) Fiber Optic Broadband Ultrasonic Probe for Virtual Biopsy: Technological Solutions. J Sensors 2010:1-6. doi: 10.1155/2010/917314
Buma T, Spisar M, O'Donnell M (2003) A high-frequency, 2-D array element using thermoelastic expansion in PDMS. IEEE Trans Ultrason Ferroelectr Freq Control 50:1161-1176.
Hou Y, Kim J J-S J-S, Ashkenazi S, et al. (2007a) Broadband all-optical ultrasound transducers. Appl Phys Lett 91:073507. doi: 10.1063/1.2771058
Hou Y, Kim J S, Ashkenazi S, et al. (2007b) All-Optical Ultrasound Transducer. Proc SPIE, Photons Plus Ultrasound Imaging Sens 6437:64370F-64370E-9. doi: 10.1117/12.698214
Hou Y, Ashkenazi S, Huang S, et al. (2007c) Integrated all-optical ultrasound transducers. IEEE Ultrason Symp 715-718.
Hou Y (2008a) Broadband all-optical ultrasound transducers for high-resolution ultrasound imaging, PhD dissertation, University of Michigan
Hou Y, Kim J S, Sheng-Wen H, et al. (2008b) Characterization of a broadband all-optical ultrasound transducer—From optical and acoustical properties to imaging. IEEE Trans Ultrason Ferroelectr Freq Control 55:1867-1877.
Hou Y, Ashkenazi S, Huang S, O' M (2008c) An integrated optoacoustic transducer combining etalon and black PDMS structures. IEEE Trans Ultrason Ferroelectr Freq Control 55:2719-2725. doi: 10.1109/TUFFC.2008.988.An
Hsieh B-Y, Chen S-L, Ling T, et al. (2012) All-optical transducer for ultrasound and photoacoustic imaging by dichroic filtering. 2012 IEEE Int Ultrason Symp 1410-1413. doi: 10.1109/ULTSYM.2012.0352
Hsieh B-Y, Chen S-L, Ling T, et al. (2014) All-optical scanhead for ultrasound and photoacoustic imaging—Imaging mode switching by dichroic filtering. Photoacoustics 2:39-46. doi: 10.1016/j.pacs.2013.12.002
Huang S-W, Ashkenazi S, Hou Y, et al. (2007) Toward fiber-based high-frequency 3D ultrasound imaging. Proc SPIE, Photons Plus Ultrasound Imaging Sens 6437:643728-643728-8. doi: 10.1117/12.701305
Li J, Taylor A, Papakonstantinou I, Zhang E and Beard P (2014) Highly sensitive optical microresonator sensors for photoacoustic imaging, Proc. of SPIE, Vol. 8943, paper 89430C
Morris P, Hurrell A, Shaw A, Zhang E, Beard P (2009) A Fabry-Pérot fiber-optic ultrasonic hydrophone for the simultaneous measurement of temperature and acoustic pressure, J. Acoust. Soc. Am. 125(6), 3611-3622
O'Donnell M, Hou Y, Kim J-S, et al. (2008) Optoacoustic generation of high frequency sound for 3-D ultrasonic imaging in medicine. Eur Phys J Spec Top 153:53-58. doi: 10.1140/epjst/e2008-00392-9
Sheaff C, Lau N, Patel H, et al. (2009) Photoacoustic imaging endoscope. Conf Proc IEEE Eng Med Biol Soc 2009:1983-6. doi: 10.1109/IEMBS.2009.5333448 [use of grin lens]
Sheaff C, Ashkenazi S (2011) An All-optical Thin-film High-frequency Ultrasound Transducer. IEEE Ultrason. Symp. 2011. pp 1944-1947
Sheaff C, Ashkenazi S (2014) Polyimide-etalon all-optical ultrasound transducer for high frequency applications. Proc SPIE, Photons Plus Ultrasound Imaging Sens 8943: 1-8. doi: 10.1117/12.2040230
Zhang E Z, Beard P C (2011) A miniature all-optical photoacoustic imaging probe, Proc. of SPIE, Vol. 7899, paper 78991F
Zou X, Wu N, Tian Y, Wang X (2014) Broadband miniature fiber optic ultrasound generator. Opt Express 22:18119. doi: 10.1364/OE.22.018119

What is claimed is:

1. A probe for ultrasound imaging of tissue, the probe comprising:
an optical relay having an optically absorbing coating at a distal end of the probe for generating ultrasound from excitation light via a photoacoustic effect, wherein the generated ultrasound propagates as an ultrasound beam into the tissue, and wherein the optical relay comprises a phased array that includes a plurality of lines that each include a plurality of fibres; and
an ultrasound receiver separate from the optical relay;
wherein the optical relay is configured to receive as an input a time-varying spatial pattern of excitation light at a proximal end of the probe that illuminates the fibres of multiple offset lines of the plurality of lines of the phased array as a first phase and then illuminates the fibers of remaining offset lines of the plurality of lines of the phased array as a second phase, and to transmit the excitation light to the distal end of the probe to illuminate the optically absorbing coating in accordance with the time-varying spatial pattern, thereby generating ultrasound from the excitation light via the photoacoustic effect to propagate and scan the ultrasound beam into the tissue, wherein the spatial pattern that is applied to the optical relay is varied in time to cause the scanning of the ultrasound beam to involve changing a profile of the beam as opposed to moving a beam of a constant profile, where the profile represents a pattern or distribution of ultrasound in a plane perpendicular to a main direction of propagation;
wherein the ultrasound receiver is configured to receive reflections of the ultrasound from tissue.

2. The ultrasound probe according to claim 1, wherein the ultrasound receiver is an electrical ultrasound transducer that comprises polyvinylidene difluoride (PVDF) or lead zirconium titanate (PZT).

3. The ultrasound probe according to claim 1, wherein the optically absorbing coating comprises an elastomer with an integrated optical absorber.

4. The ultrasound probe according to claim 1, further comprising an acoustic lens positioned distal to the optically absorbing coating to provide an ultrasound focus.

5. The ultrasound probe of claim 1, further comprising at least one ultrasonically reflective element to deflect generated ultrasound.

6. The ultrasound probe according to claim 1, further comprising at least one channel for communicating fluid from a point of injection at the proximal end to a region surrounding the distal end.

7. The ultrasound probe according to claim 1, wherein the ultrasound receiver includes an optical light guide, separate from said optical relay, and further includes an ultrasound-sensitive optical element at the distal end of the probe, the ultrasound-sensitive optical element having a reflectivity that is modulated by ultrasound impinging on said optical element;
wherein the ultrasound-sensitive optical element is configured to receive ultrasound reflections from tissue during the scanning of the ultrasound beam generated by the optically absorbing coating;
and wherein the optical light guide is configured to convey interrogation light onto the optical element and to convey reflected light back from the optical element, said reflected light being modulated in accordance said ultrasound reflections from tissue.

8. The ultrasound probe of claim 7, wherein the ultrasound- sensitive optical element is wavelength-selective, so as to be reflective at the wavelength of said interrogation light, but transmissive at a second wavelength to allow a light of the second wavelength from the optical light guide to pass into the tissue.

9. The ultrasound probe according to claim 7, wherein the ultrasound-sensitive optical element is a Fabry-Pérot cavity which has two reflective coatings.

10. The ultrasound probe according to claim 9, wherein the two reflective coatings in the Fabry-Pérot cavity are dielectric.

11. The ultrasound probe according to claim 9, wherein a distal one of the two reflective coatings in the Fabry-Pérot cavity is convex.

12. The ultrasound probe according to claim 1, wherein there is at least one ultrasound attenuating component positioned between the ultrasound receiver and the optically absorbing coating, wherein the ultrasound attenuating component acts to reduce the amplitude of ultrasound waves that propagate directly from the optically absorbing coating to the ultrasound receiver.

13. The ultrasound probe according to claim 12, wherein the ultrasound attenuating component is a metal hypotube.

14. The ultrasound probe according to claim 1, wherein said spatial pattern of the excitation light is spatially transformed within the ultrasound probe from a first pattern which emerges from the optical relay to a second pattern which illuminates the optically absorbing coating.

15. The ultrasound probe according to claim 14, wherein the spatial transformation includes an angular deflection of excitation light away from the longitudinal axis of the ultrasound probe.

16. The ultrasound probe according to claim 15, wherein the optically absorbing coating is parallel to the longitudinal axis of the ultrasound probe.

17. The ultrasound probe according to claim 1, in which the surface of the optically absorbing coating has a curvature.

18. The ultrasound probe according to claim 17, in which said curvature is concave in one dimension to provide an ultrasound focus for the ultrasound beam.

19. The ultrasound probe according to claim 17, in which said curvature is convex to diverge the ultrasound beam.

20. The ultrasound probe of according to claim 1, wherein the optical absorbing coating is wavelength-selective, and is absorbing at the wavelength of said excitation light, but is transmissive at a second wavelength to allow a light of the second wavelength from the optical relay to pass into the tissue.

21. The ultrasound probe of claim 20, wherein light of the second wavelength is used for generating ultrasound in tissue using the photoacoustic effect, and wherein the ultrasound receiver is configured to receive reflections of the transmitted ultrasound from the tissue.

22. The ultrasound probe of claim 20, wherein light of the second wavelength is used for generating fluorescence in tissue.

23. The ultrasound probe according to claim 1, wherein the optical relay comprises an optical fibre bundle that includes the plurality of lines that each include the plurality of fibres.

24. The ultrasound probe according to claim 23, wherein the optical fibre bundle is coherent, so that the relative spatial positioning of individual fibres within the optical fibre bundle is the same at the distal end as at the proximal end.

* * * * *